US009346751B2

(12) United States Patent
Beliaev et al.

(10) Patent No.: US 9,346,751 B2
(45) Date of Patent: May 24, 2016

(54) PROCESS FOR PREPARING 1, 3-DIHYDROIMIDAZOLE-2-THIONE DERIVATIVES

(75) Inventors: Alexander Beliaev, S. Mamede do Coronado (PT); Jorge Bruno Reis Wahnon, S. Mamede do Coronado (PT); David Alexander Learmonth, Alfena (PT); Jonathan Madec, Chatou (FR); Jean-Marie Schneider, Magnanville (FR); William Maton, S. Mamede do Coronado (PT)

(73) Assignee: Bial-Portela & CA, S.A., S. Mamede do Coronado (PT)

( * ) Notice: Subject to any disclaimer, the term of this patent is extended or adjusted under 35 U.S.C. 154(b) by 16 days.

(21) Appl. No.: 14/127,231

(22) PCT Filed: Jun. 29, 2012

(86) PCT No.: PCT/PT2012/000024
§ 371 (c)(1),
(2), (4) Date: Apr. 7, 2014

(87) PCT Pub. No.: WO2013/002660
PCT Pub. Date: Jan. 3, 2013

(65) Prior Publication Data
US 2014/0221668 A1 Aug. 7, 2014

Related U.S. Application Data

(60) Provisional application No. 61/502,647, filed on Jun. 29, 2011.

(51) Int. Cl.
*C07D 405/04* (2006.01)
*C07C 311/17* (2006.01)
*C07C 311/16* (2006.01)
*C07C 235/80* (2006.01)

(52) U.S. Cl.
CPC ............. *C07C 311/17* (2013.01); *C07C 235/80* (2013.01); *C07C 311/16* (2013.01); *C07D 405/04* (2013.01)

(58) Field of Classification Search
CPC .................................................. C07D 405/04
See application file for complete search history.

(56) References Cited

U.S. PATENT DOCUMENTS 8,481,582 B2    7/2013  Soares Da Silva et al.

FOREIGN PATENT DOCUMENTS

WO           9529165 A2    11/1995
WO        2004033447 A1     4/2004
WO        2008136695 A1    11/2008
WO        2013002660 A2     1/2013
WO        2013002660 A3     1/2013

OTHER PUBLICATIONS

Beliaev, Alexandre, et al., "Synthesis and Biological Evaluation of Novel, Peripherally Selective Chromanyl Imidazolethione-Based Inhibitors of Dopamine B-Hydroxylase," XP-002476679, J. Med. Chem., 2006, vol. 49, No. 3, pp. 1191-1197, American Chemical Society.
Benedict, Claude R., et al., "Prognostic Significance of Plasma Norepinephrine in Patients with Asymptomatic Left Ventricular Dysfunction," Circulation, Aug. 15, 1996, vol. 94, No. 4, pp. 690-697, American Heart Association, Inc.
Cohn, Jay N., et al., "Plasma Norepinephrine as a Guide to Prognosis in Patients with Chronic Congestive Heart Failure," The New England Journal of Medicine, Sep. 27, 1984, vol. 311, No. 13, pp. 819-823, Massachusetts Medical Society.
Foreign communication from the priority application—International Search Report and Written Opinion, PCT/PT2012/000024, Jan. 23, 2013, 16 pages.
Goldstein, Menek, et al., "Inhibition of Dopamine-B-Hydroxylase by Disulfiram," Life Sciences, 1964, vol. 3, No. 7, pp. 763-767, Pergamon Press, Inc.
Hasking, Gregory J., et al., "Norepinephrine spillover to plasma in patients with congestive heart failure: evidence of increased overall and cardiorenal sympathetic nervous activity," Circulation, Apr. 1986, vol. 73, No. 4, pp. 615-621.
Hidaka, Hiroyoshi, Fusaric (5-Butylpicolinic) Acid, an Inhibitor of Dopamine B-Hydroxylase, affects Serotonin and Noradrenaline, Nature, May 7, 1971, vol. 231, pp. 54-55.
Johnson, G. A., et al., "In Vivo Inhibition of Dopamine B-Hydroxylase by 1-Phenyl-3-(2-Thiazolyl)-2-Thiourea (U-14,624)," The Journal of Pharmacology and Experimental Therapeutics, 1970, vol. 171, No. 1, pp. 80-87, The Williams & Wilkins Co.
Leimbach, Jr., Wayne N., et al., "Direct evidence from intraneural recordings for increased central sympathetic outflow in patients with heart failure," Circulation, May 1986, vol. 73, No. 5, pp. 913-919.
Levine, T. Barry, et al., "Activity of the Sympathetic Nervous System and Renin-Angiotensin System Assessed by Plasma Hormone Levels and Their Relation to Hemodynamic Abnormalities in Congestive Heart Failure," The American Journal of Cardiology, May 1982, vol. 49, pp. 1659-1666.
Lippmann, W., et al., "Dopamine-B-Hydroxylase Inhibition by Dimethyldithiocarbamate and Related Compounds," 1969, pp. 2507-2516.
Parmley, William W., "Neuroendocrine Changes in Heart Failure and Their Clinical Relevance," Clin. Cardiol., Aug. 1995, vol. 18, pp. 440-445.
Pfeffer, Marc A., et al., "B-Adrenergic Blockers and Survival in Heart Failure," The New England Journal of Medicine, May 23, 1996, vol. 334, No. 21, pp. 1396-1397, Massachusetts Medical Society.

(Continued)

*Primary Examiner* — Shawquia Jackson
(74) *Attorney, Agent, or Firm* — Conley Rose, P.C.; Rodney B. Carroll

(57) ABSTRACT

The present invention relates to a process for preparing (R)-5-(2-(benzylamino)ethyl)-1-(6,8-difluorochroman-3-yl)-1H-imidazole-2(3H)-thione, and pharmaceutically acceptable salts thereof, especially the hydrochloride salt. The invention also relates to a process for making intermediates useful in the formation of said compound, and to the intermediates, per se.

20 Claims, No Drawings

(56) References Cited

OTHER PUBLICATIONS

Stanley, William C., et al., "Catecholamine modulatory effects of nepicastat (RS-25560-197), a novel, potent and selective inhibitor of dopamine-B-Hydroxylase," British Journal of Pharmacology, 1997, vol. 121, pp. 1803-1809, Stockton Press.

American Psychiatric Association, "Diagnostic and Statistical Manual of Mental Disorders," Fourth Edition, Text Revision, 2000, pp. 429-484 plus 2 pages cover and publishing information.

Filing receipt and specification for provisional patent application entitled "Process," by Alexander Beliaev, et al., filed Jun. 29, 2011 as U.S. Appl. No. 61/502,647.

Foreign communication from the priority application—International Preliminary Report on Patentability, PCT/PT2012/000024, Jan. 7, 2014, 11 pages.

PROCESS FOR PREPARING 1, 3-DIHYDROIMIDAZOLE-2-THIONE DERIVATIVES

CROSS-REFERENCE TO RELATED APPLICATIONS

This application is a filing under 35 U.S.C. 371 of International Application No. PCT/PT2012/000024 filed Jun. 29, 2012, entitled "Process," which claims priority to U.S. Provisional Patent Application No. 61/502,647 filed Jun. 29, 2011, which applications are incorporated by reference herein in their entirety.

FIELD OF INVENTION

The present invention relates to a process for preparing ®-5-(2-(benzylamino)ethyl)-1-(6,8-difluorochroman-3-yl)-1H-imidazole-2(3H)-thione, and pharmaceutically acceptable salts thereof, especially the hydrochloride salt. The invention also relates to a process for making intermediates useful in the formation of said compound, and to the intermediates, per se.

BACKGROUND OF THE INVENTION

In recent years, interest in the development of inhibitors of dopamine-β-hydroxylase (DβH) has centred on the hypothesis that inhibition of this enzyme may provide significant clinical improvements in patients suffering from cardiovascular disorders such as hypertension or chronic heart failure. The rationale for the use of DβH inhibitors is based on their capacity to inhibit the biosynthesis of noradrenaline, which is achieved via enzymatic hydroxylation of dopamine. Activation of neurohumoral systems, chiefly the sympathetic nervous system, is the principal clinical manifestation of congestive heart failure (Parmley, W. W., Clinical Cardiology, 18: 440-445, 1995). Congestive heart failure patients have elevated concentrations of plasma noradrenaline (Levine, T. B. et al., Am. J. Cardiol., 49:1659-1666, 1982), increased central sympathetic outflow (Leimbach, W. N. et al., Circulation, 73: 913-919, 1986) and augmented cardiorenal noradrenaline spillover (Hasking, G. J. et al., Circulation, 73:615-621, 1966). Prolonged and excessive exposure of the myocardium to noradrenaline may lead to down-regulation of cardiac $\beta_1$-adrenoceptors, remodelling of the left ventricle, arrhythmias and necrosis, all of which can diminish the functional integrity of the heart. Congestive heart failure patients who have high plasma concentrations of noradrenaline also have the most unfavourable long-term prognosis (Cohn, J. N. et al., N. Engl. J. Med., 311:819-823, 1984). Of greater significance is the observation that plasma noradrenaline concentrations are already elevated in asymptomatic patients with no overt heart failure and can predict ensuing mortality and morbidity (Benedict, C. R. et al., Circulation, 94:690-697, 1996). An activated sympathetic drive is not therefore merely a clinical marker of congestive heart failure, but may contribute to progressive worsening of the disease.

Inhibition of sympathetic nerve function with adrenoceptor antagonists appeared a promising approach, however a significant proportion of patients do not tolerate the immediate haemodynamic deterioration that accompanies p-blocker treatment (Pfeffer, M. A. et al., N. Engl. J. Med., 334:1396-7, 1996). An alternative strategy for directly modulating sympathetic nerve function is to reduce the biosynthesis of noradrenaline via inhibition of DβH, the enzyme responsible for conversion of dopamine to noradrenaline in sympathetic nerves. This approach has several advantages including gradual modulation as opposed to abrupt inhibition of the sympathetic system, and increased release of dopamine, which can improve renal function such as renal vasodilation, diuresis and natriuresis. Therefore, inhibitors of DβH may provide significant advantages over conventional β-blockers.

Several inhibitors of DβH have been thus far reported in the literature. Early first and second generation examples such as disulfuram (Goldstein, M. et al., Life Sci., 3:763, 1964) and diethyldithiocarbamate (Lippmann, W. et al., Biochem. Pharmacol., 18: 2507, 1969) or fusaric acid (Hidaka, H. Nature, 231, 1971) and aromatic or alkyl thioureas (Johnson, G. A. et al, J. Pharmacol. Exp. Ther., 171: 80, 1970) were found to be of low potency, exhibited poor selectivity for DβH and caused toxic side effects. The third generation of DβH inhibitors however, were found to have much greater potency, such as for example, nepicastat (RS-25560-197, IC$_{50}$ 9 nM) (Stanley, W. C., et al., Br. J. Pharmacol., 121: 1803-1809, 1997), which was developed to early clinical trials. Although devoid of some of the problems associated with first and second generation DβH inhibitors, a very important discovery was that nepicastat was found to cross the blood brain barrier (BBB), and was thereby able to cause central as well as peripheral effects, a situation which could lead to undesired and potentially serious CNS side-effects of the drug. Therefore, there remains an unfulfilled clinical requirement for a potent, non-toxic and peripherally selective inhibitor of DβH, which could be used for treatment of certain cardiovascular disorders. A DβH inhibitor with similar or even greater potency than nepicastat, but devoid of CNS effects (inability to cross the BBB) would provide a significant improvement over all DβH inhibitor compounds thus far described in the prior art.

Dopamine-β-hydroxylase inhibitors are also disclosed in WO95/29165. Furthermore, WO 2004/033447 discloses dopamine-β-hydroxylase inhibitors having high potency and significantly reduced brain access, giving rise to potent and peripherally selective DβH inhibitors.

WO2008/136695 discloses a compound of formula I:

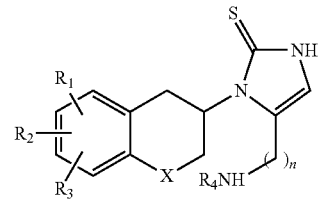

where R$_1$, R$_2$ and R$_3$ are the same or different and signify hydrogens, halogens, alkyl, nitro, amino, alkylcarbonylamino, alkylamino or dialkylamino group; R$_4$ signifies -alkylaryl or -alkylheteroaryl; X signifies CH$_2$, oxygen atom or sulphur atom; and n is 2 or 3. WO2008/136695 also discloses a compound of formula Y, its (R) or (S) enantiomer, or mixture of (R) and (S) enantiomer, or pharmaceutically acceptable salts or esters thereof.

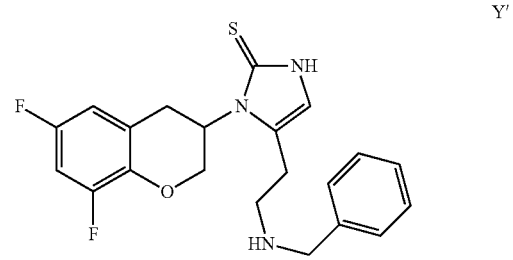 [SMILES: Fc1cc(F)c2c(c1)CC(n1c(CCNCc3ccccc3)c[nH]c1=S)CO2]

SUMMARY OF THE INVENTION

We have now found new processes for preparing inter alia compounds of formula Y'.

The present invention provides processes for preparing a compound of formula RY', which is the R-enantiomer of compound Y'. The present invention also relates to derivatives of compound RY', which derivatives have the formula RY.

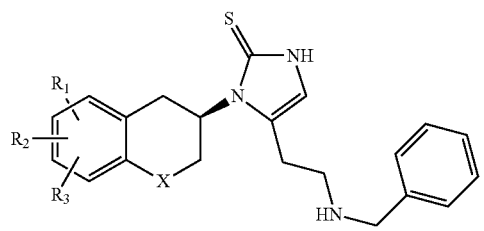

RY

The present invention also provides intermediates for use in the processes, and processes for preparing and using the intermediates.

DETAILED DESCRIPTION OF THE INVENTION

According to a first aspect of the present invention, there is provided a process for preparing a compound of formula RY or a pharmaceutically acceptable salt thereof,

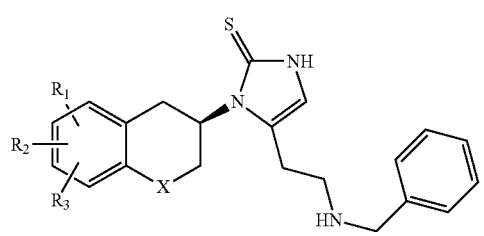

RY wherein, $R_1$, $R_2$ and $R_3$ are the same or different and signify hydrogen, halogen, alkyl, nitro, amino, alkylcarbonylamino, alkylamino or dialkylamino group; and
X signifies $CH_2$, oxygen atom or sulphur atom;
which process comprises reducing a compound of formula D,

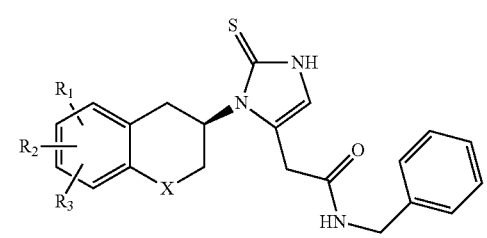

D wherein $R_1$, $R_2$, $R_3$ and X are as hereinbefore defined in formula RY;
and optionally thereafter converting the compound RY to a pharmaceutically acceptable salt thereof.

According to a preferred embodiment of the present invention, the compound of formula D is prepared by condensing a compound of formula C,

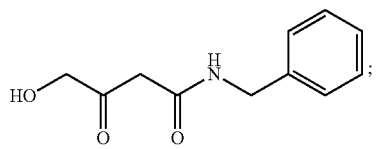

C with a compound of formula JT,

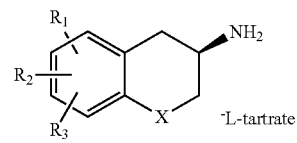

JT wherein $R_1$, $R_2$, $R_3$ and X are as hereinbefore defined in formula RY.

According to a further preferred embodiment of the invention, the compound of formula C is prepared by hydroxylating a compound of formula B,

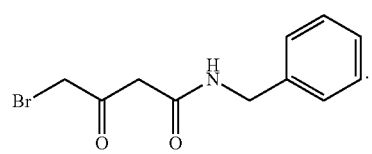

B

According to a still further preferred embodiment of the invention, the compound of formula B is prepared brominating a compound of formula A,

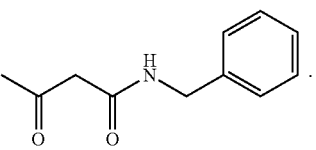

A

A particularly preferred process for preparing a compound of formula RY according to the present invention is as shown in Scheme 1.

Scheme 1

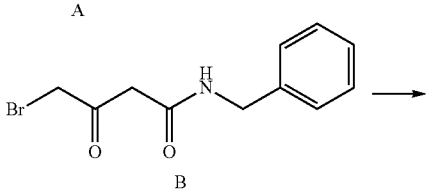

-continued

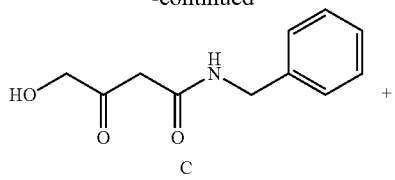
C

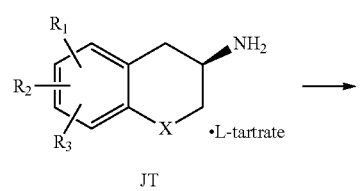
JT

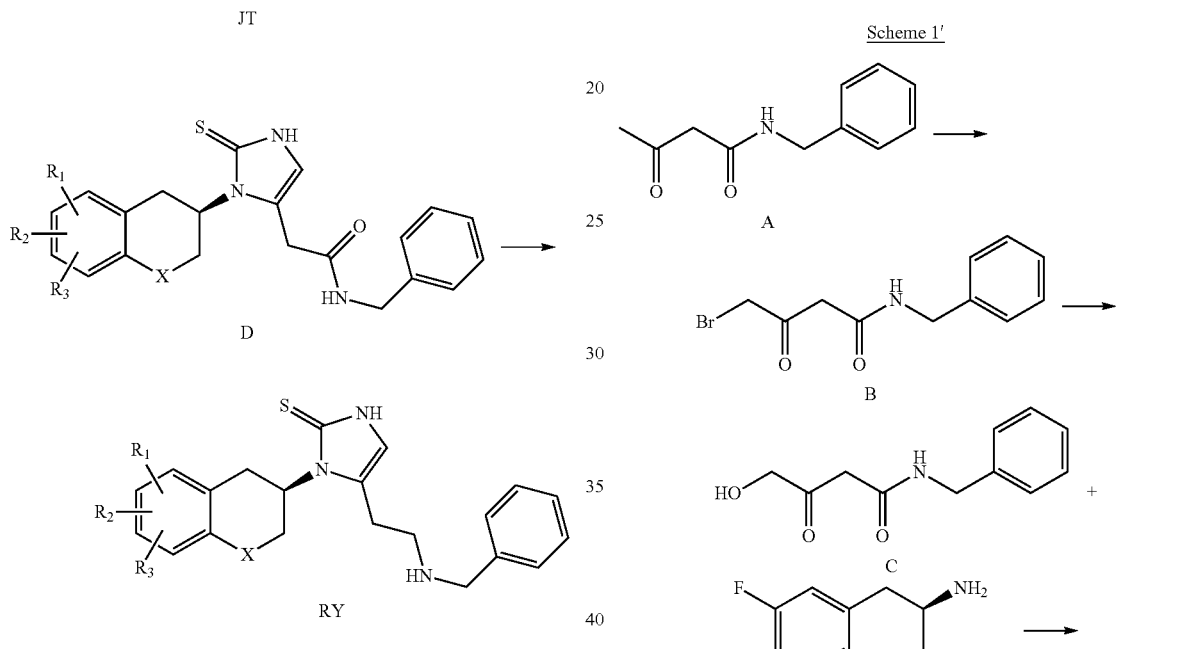

The process comprises: brominating a compound of formula A to form a compound of formula B; hydroxylating a compound B to a compound of formula C; condensing the compound C with a compound of formula JT to form a compound of formula D; and reducing the compound D to form the compound of formula RY, and optionally converting compound RY to a pharmaceutically acceptable salt thereof; where $R_1$, $R_2$ and $R_3$ are the same or different and signify hydrogen, halogen, alkyl, nitro, amino, alkylcarbonylamino, alkylamino or dialkylamino group; and X signifies $CH_2$, oxygen atom or sulphur atom.

As used herein the term "alkyl" means hydrocarbon chains, straight or branched, containing from one to six carbon atoms, optionally substituted by aryl, alkoxy, halogen, alkoxycarbonyl or hydroxycarbonyl groups.

As used herein, the term "aryl" means a phenyl or naphthyl group, optionally substituted by alkyl, alkyloxy, halogen or nitro group.

As used herein, the term "halogen" means fluorine, chlorine, bromine or iodine; the term heteroaryl means heteroaromatic group.

In an embodiment, X is O.

In an embodiment, one of $R_1$, $R_2$ and $R_3$ is hydrogen, and the others are fluorine.

In an embodiment, compound RY has the formula RY'

and the process is as defined in Scheme 1' below.

Scheme 1'

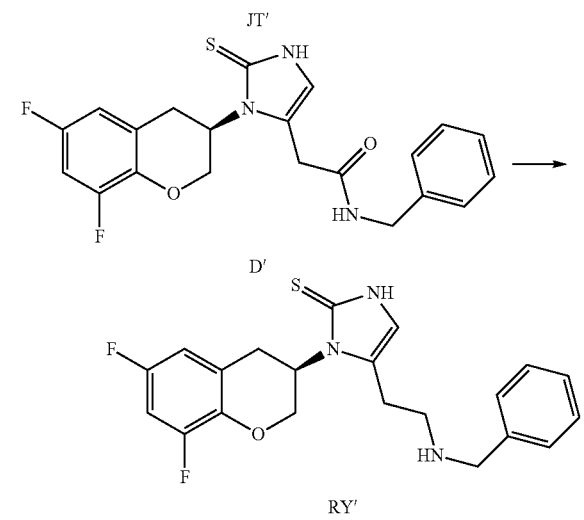

The brominating step is carried out in the presence of a suitable brominating reagent such as N-bromosuccinimide (NBS), dibromohydantoin or bromine. In a preferred embodiment, the brominating step is carried out in the presence of bromine. Suitably, the bromination is carried out at a temperature ranging from about 0° C. to about 25° C., preferably from about 0° C. to about 5° C. Preferably, the reaction mixture is heated to room temperature, i.e. around 25° C., after addition of bromine. It has been observed that the bromination reaction may result in a mixture of isomers. In such circumstances, the process may further comprise treating of the bromination product B (suitably after filtration thereof with DCM) with a suitable aqueous base such as aqueous bicarbonate solution, followed by extraction with a suitable solvent such as methyl tert-butyl ether (MTBE) and crystallization from a further suitable solvent such as MTBE.

In an embodiment, the conversion of the bromide B to the hydroxy ketone C is achieved by treatment with an alkaline metal formate, preferably sodium, potassium or cesium formate, most preferably potassium formate in a suitable solvent such as methanol, preferably boiling methanol. For this step, crude bromide of formula B may be used without purification (i.e. either as the HBr salt or as the free base). Advantageously, the hydroxy ketone C was observed to be obtained as a stable crystalline material. Preferably, the reaction temperature is about 50° C. or higher, more preferably from about 50° C. to the reflux temperature of the solvent used. Most preferably, the reaction is carried out under reflux.

When the HBr salt is used for the conversion, the alkaline metal formate is present in at least 3 molar equivalents. When the free base is used for the conversion, the alkaline metal formate is present in at least 2 molar equivalents.

Cyclisation of the hydroxy ketone C with compound JT is preferably carried out using an alkali metal thiocyanate such as potassium thiocyanate and a suitable acid such as acetic acid (AcOH) in a suitable solvent such as 2-propanol. Advantageously, the use of 2-propanol avoids the need for chromatographic purification of compound D.

In an embodiment, the reduction of compound D to the target material compound RY is carried out using a reducing agent comprising $NaBH_4$—$BF_3$. complex such as $NaBH_4$—$BF_3.Et_2O$, $NaBH_4$—$BF_3.THF$, preferably $NaBH_4$—$BF_3.THF$ in a suitable solvent such as THF or Me-THF, preferably THF (it is believed that this results in in situ borane formation). Suitable amounts of reducing agent are 5 or 2.5 molar equivalents of each or 2.5 molar equivalents of $NaBH_4$ with 3.3 molar equivalents of $BF_3.Et_2O$ or $BF_3.THF$, preferably 2.5 molar equivalents of $NaBH_4$ with 3.3 molar equivalents of $BF_3.THF$. Alternative reducing agents are sodium bis(methoxyethoxy)aluminohydride) (RedAl™), Borane-THF complex (BTHF) and $NaBH_4$-methanesulfonic acid.

In an embodiment, the process further comprises converting the compound RY to a pharmaceutically acceptable salt thereof. Suitable pharmaceutically acceptable salts include acid addition salts. Preferably, the pharmaceutically acceptable salt is the HCl salt.

It will be appreciated that several of the intermediates for use in the process are novel and inventive, as are the processes for preparing them and the processes involving their use. These intermediates and processes form further aspects of the present invention, as is described below.

According to another aspect of the present invention, there is provided a compound of formula B

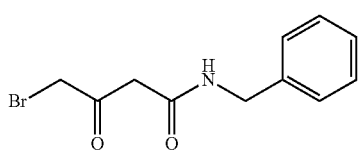

B

According to another aspect of the present invention, there is provided a process for preparing a compound of formula B. The process is as described above.

According to another aspect of the present invention, there is provided a process for preparing a compound of formula C from the compound of formula B. The process is as described above. The present invention also provides the use of compound B in a process for preparing (R)-5-(2-(benzylamino)ethyl)-1-(6,8-difluorochroman-3-yl)-1H-imidazole-2(3H)-thione, or a pharmaceutically acceptable salt thereof, especially the hydrochloride salt.

According to another aspect of the present invention, there is provided a compound of formula C

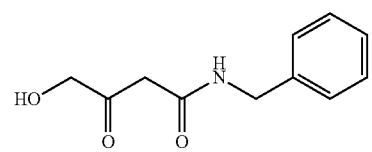

C

According to another aspect of the present invention, there is provided a process for preparing a compound of formula C. The process is as described above.

According to another aspect of the present invention, there is provided a process for preparing a compound of formula D from the compound of formula C. The process is as described above. The present invention also provides the use of compound C in a process for preparing (R)-5-(2-(benzylamino)ethyl)-1-(6,8-difluorochroman-3-yl)-1H-imidazole-2(3H)-thione, or a pharmaceutically acceptable salt thereof, especially the hydrochloride salt.

According to another aspect of the present invention, there is provided a compound of formula D

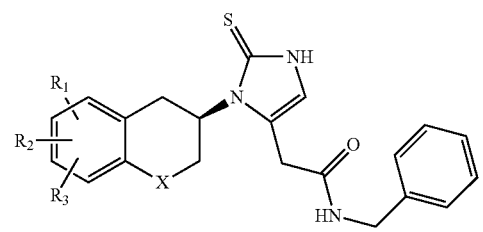

D where $R_1$, $R_2$ and $R_3$ are the same or different and signify hydrogen, halogen, alkyl, nitro, amino, alkylcarbonylamino, alkylamino or dialkylamino group; and X signifies $CH_2$, oxygen atom or sulphur atom; wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyl, alkyloxy, halogen or nitro group; the term halogen means fluorine, chlorine, bromine or iodine; the term heteroaryl means heteroaromatic group.

In an embodiment, X is O.

In an embodiment, one of $R_1$, $R_2$ and $R_3$ is hydrogen, and the others are fluorine.

In an embodiment, compound D has the formula D'

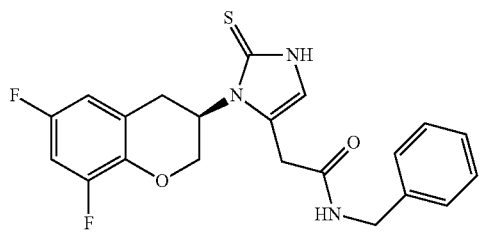

According to another aspect of the present invention, there is provided a process for preparing a compound of formula D. The process is as described above.

According to another aspect of the present invention, there is provided a process for preparing a compound of formula RY from the compound of formula D. The process is as described above. The present invention also provides the use of compound D in a process for preparing (R)-5-(2-(benzylamino)ethyl)-1-(6,8-difluorochroman-3-yl)-1H-imidazole-2(3H)-thione, or a pharmaceutically acceptable salt thereof, especially the hydrochloride salt. Preferably, the compound D' is used to prepare the compound RY'.

According to another aspect of the present invention, there is provided a process for preparing a compound of formula RY or a pharmaceutically acceptable salt thereof,

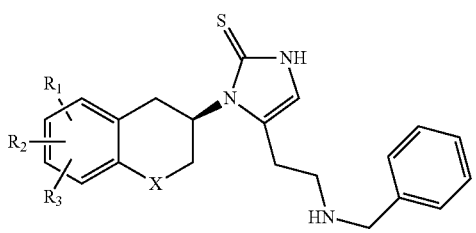

wherein, $R_1$, $R_2$ and $R_3$ are the same or different and signify hydrogen, halogen, alkyl, nitro, amino, alkylcarbonylamino, alkylamino or dialkylamino group; and
X signifies $CH_2$, oxygen atom or sulphur atom;
which process comprises deprotecting a compound of formula K

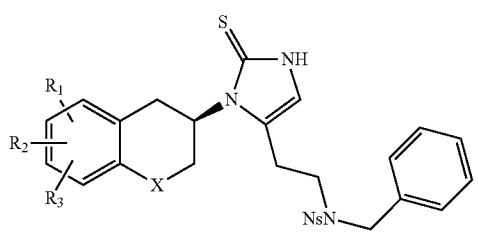

wherein $R_1$, $R_2$, $R_3$ and X are as hereinbefore defined in formula RY and Ns signifies o-nitrophenylsulphonyl;
and optionally thereafter converting the compound RY to a pharmaceutically acceptable salt thereof.

According to a preferred embodiment of the present invention, the compound of formula K is prepared by reacting a compound of formula I,

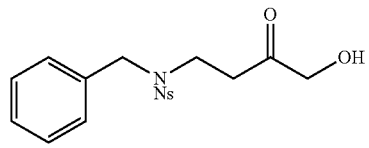

wherein Ns signifies o-nitrophenylsulphonyl;
with a compound of formula JZ,

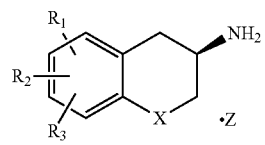

wherein $R_1$, $R_2$, $R_3$ and X are as hereinbefore defined in formula RY, X signifies $CH_2$, an oxygen atom or a sulphur atom, and Z is selected from L-tartrate, hydrochloride, mesylate, tosylate, trifluotoacetate, citrate, glycolate and oxalate.

According to a further preferred embodiment of the present invention, the compound of formula I is prepared by hydroxylating a compound of formula G

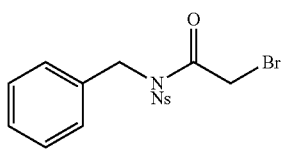

wherein Ns signifies o-nitrophenylsulphonyl.

According to a further preferred embodiment of the present invention, the compound of formula I is prepared by hydrolysing a compound of formula H,

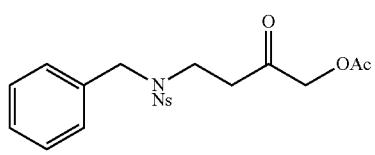

wherein Ns signifies o-nitrophenylsulphonyl.

According to a further preferred embodiment of the present invention, the compound of formula H is prepared by acylating a compound of formula G,

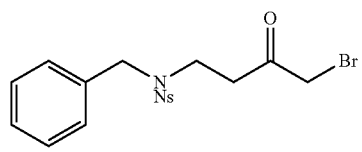

wherein Ns signifies o-nitrophenylsulphonyl.

According to a still further preferred embodiment of the present invention, the compound of formula G is prepared by brominating a compound of formula F,

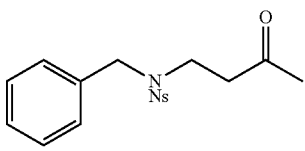

F wherein Ns signifies o-nitrophenylsulphonyl.

According to a still further preferred embodiment of the present invention, the compound of formula F is prepared by reacting a compound of formula E,

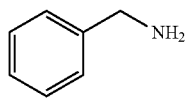

E with o-nitrophenylsuplonyl chloride.

A particularly preferred process for preparing a compound of formula RY according to the present invention is as shown in Scheme 2.

The process comprises: converting benzylamine E to a compound of formula F in the presence of o-nitrophenylsulphonyl chloride and a suitable solvent such as methyl vinyl ketone (MVK); converting the compound F to a compound of formula G in the presence of a brominating agent; hydroxylating a compound G to a compound of formula I or acetylating compound G to form a compound of formula H followed by hydrolysing the compound H to form a compound of formula I; reacting the compound I with a compound of formula JZ to form a compound of formula K; and deprotecting compound K to form compound RY, where Ns is o-nitrophenylsulphonyl, Z is selected from L-tartrate, hydrochloride, mesylate, tosylate, trifluotoacetate, citrate, glycolate and oxalate, $R_1$, $R_2$ and $R_3$ are the same or different and signify hydrogen, halogen, alkyl, nitro, amino, alkylcarbonylamino, alkylamino or dialkylamino group; and X signifies $CH_2$, oxygen atom or sulphur atom.

In an embodiment, X is O.

In an embodiment, one of $R_1$, $R_2$ and $R_3$ is hydrogen, and the others are fluorine.

In an embodiment, Z is L-tartrate. In this embodiment, compound JZ has the formula JT and compound JZ' has the formula JT'.

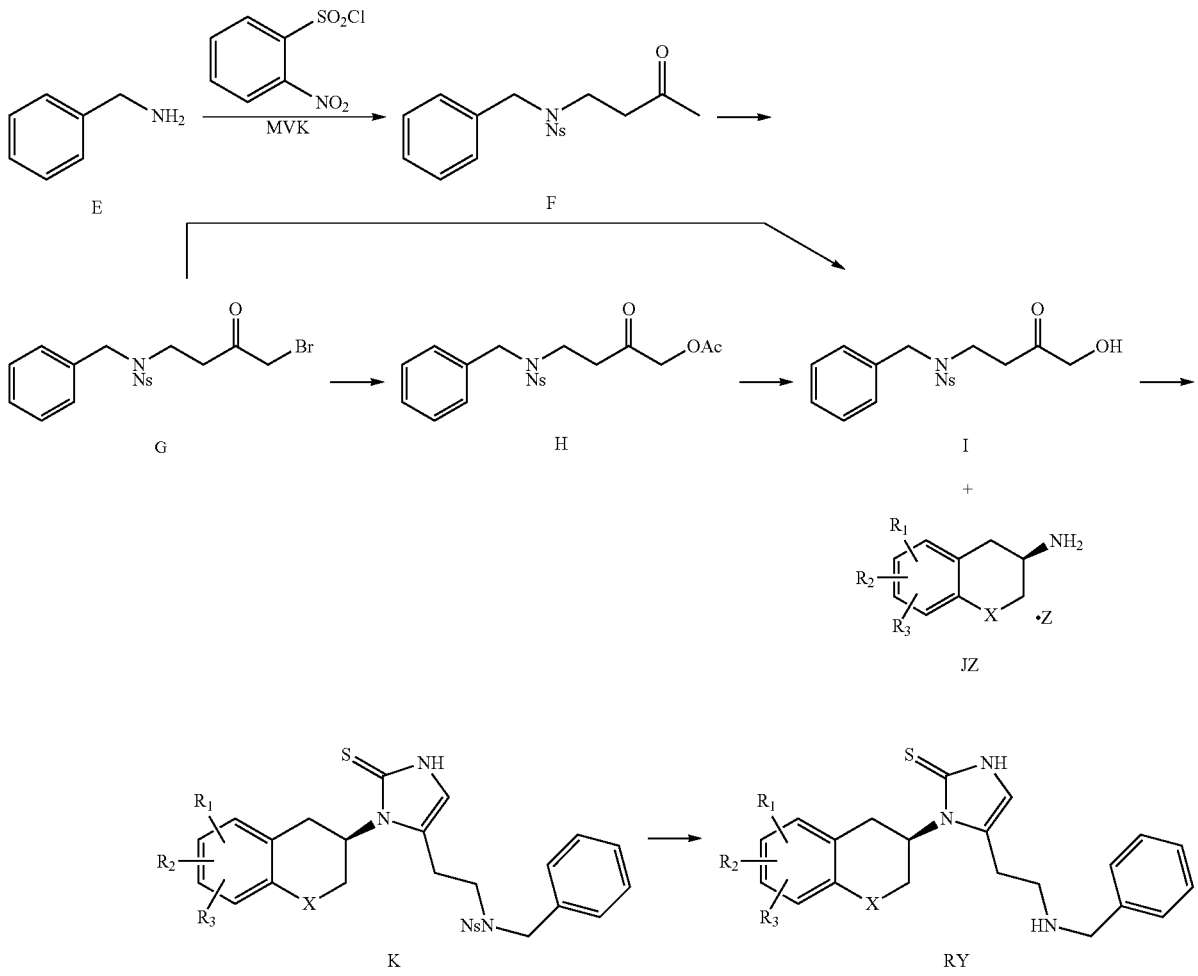

Scheme 2

13
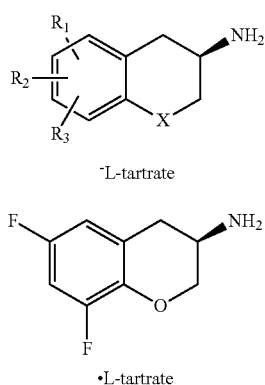
14
In an embodiment, compound RY has the formula RY'
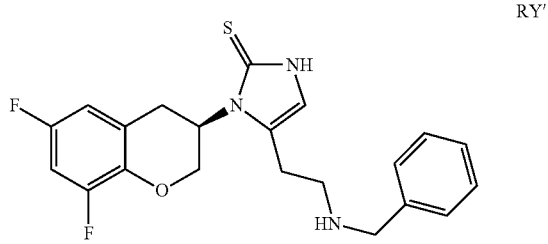 [SMILES: Fc1cc(F)c2c(c1)C[C@@H](n1c(CCNCc3ccccc3)c[nH]c1=S)CO2]
and the process is as defined in Scheme 2' below.
Scheme 2'
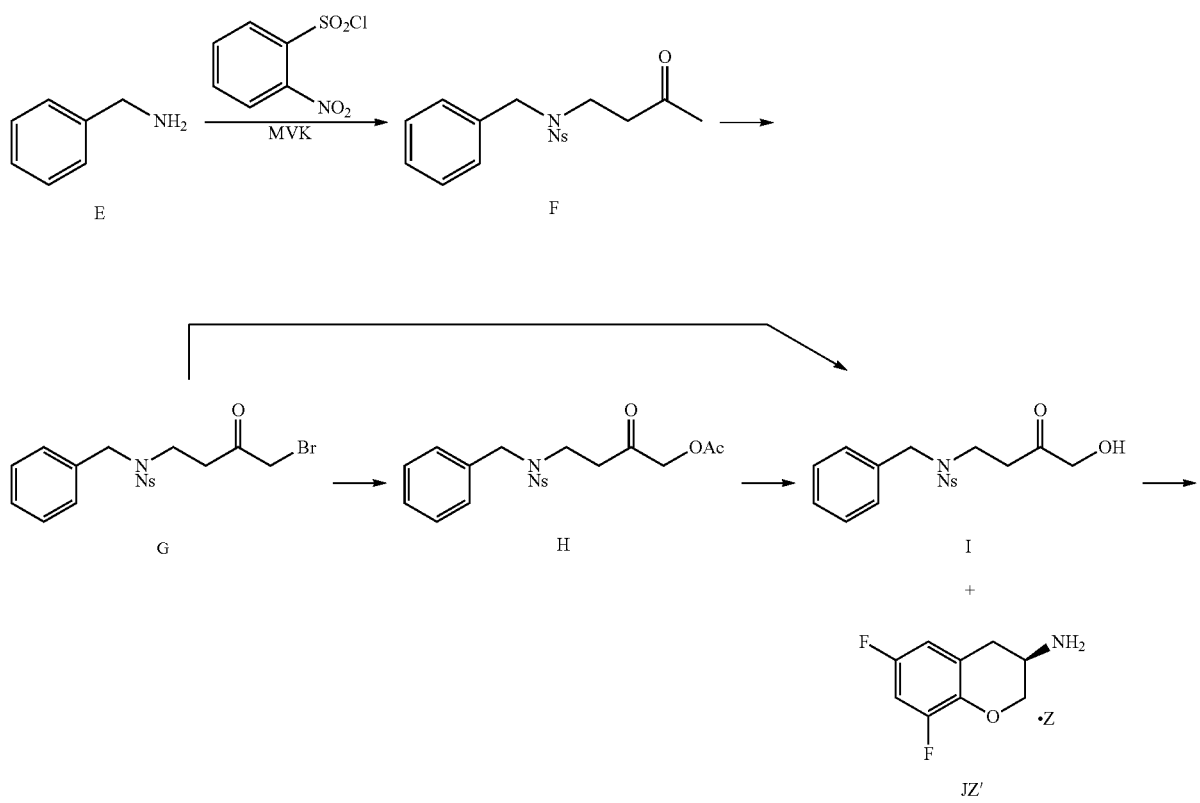
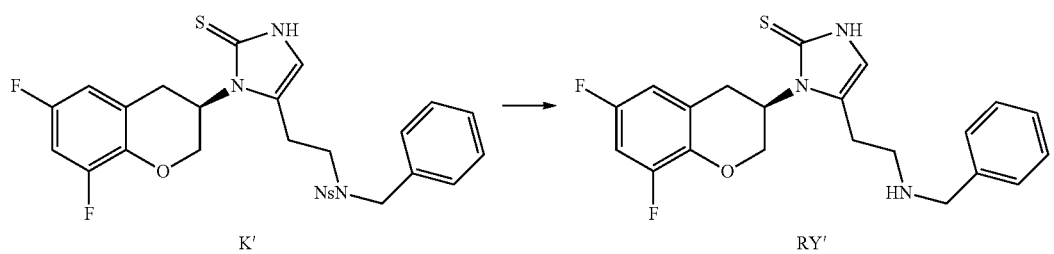

In an embodiment, the conversion of compound E to compound F is carried out in the presence of a base such as triethylamine, tributylamine, diisopropylethylamine, N-methyl morpholine, preferably triethylamine and a catalytic amount of a suitable alkali metal alkoxide such as potassium tert-butoxide (t-BuOK), sodium methoxide, sodium ethoxide or sodium tert-butoxide, preferably, potassium tert-butoxide.

In an embodiment, the bromination of compound F is achieved using $Br_2$ in the presence of MeOH.

In an embodiment, the acetylation of compound G is achieved using an alkaline metal acetate, such as potassium acetate (KOAc), sodium acetate or cesium acetate, preferably potassium acetate, in the presence of a suitable acid such as acetic acid (AcOH).

In an embodiment, the hydrolysis of compound H is achieved using a suitable acid such as HCl in the presence of a suitable solvent such as 2-propanol.

In an embodiment, the hydroxylation of compound G to a compound of formula I is achieved by treatment with an alkaline metal formate, such as sodium, potassium or cesium formate, preferably potassium formate in presence of formic acid in methanol. Suitably, the reaction temperature is about 50° C. or higher, preferably from about 50° C. to the reflux temperature of the solvent used. Most preferably, the reaction is carried out under reflux. Advantageously, the compound of formula I was obtained in one step procedure from compound G.

In an embodiment, the condensation of compounds I and JZ is carried out in the presence of an alkaline metal thiocyanate, such as potassium thiocyanate (KSCN), sodium thiocyanate and cesium thiocyanate, preferably potassium thiocyanate or an tetraalkylammonium thiocyanate, such as tetrabutylammonium thiocyanate and an acid, such as acetic acid (AcOH) or propionic acid, preferably AcOH. In another embodiment, compound I can be condensed with the hydrochloride, mesylate, tosylate, trifluotoacetate, citrate, glycolate or oxalate salt equivalents of compound J as described above.

In an embodiment, deprotection of the nosyl compound K is achieved with thioglycolic acid in a polar aprotic solvent such as DMF, DMSO and NMP, preferably DMSO or DMF in the presence of a base, suitably LiOH, NaOH, KOH, CsOH or quaternary ammonium hydroxides, such as tetrabutylammonium hydroxide, preferably LiOH or KOH. Suitably, the deprotection is carried out at room temperature, i.e. about 25° C. or at about 40° C. Advantageously, the isolated yield of compound RY ranges from 91% to 96% and HPLC has shown the purity of the crude product to be around 98% area (Kromasil 100 5C4 250×4.6 column, mobile phase 0.1% TFA-ACN 25:75 at 1 ml/min, 270 nm).

In an embodiment, the compound RY isolated from the deprotection step is then purified. In an embodiment, the purification is performed via a two-step procedure comprising formation of the HCl salt in MeOH with methanolic HCl and crystallisation of the HCl salt of compound RY from toluene after removal of MeOH, followed by isolation of the compound RY in free base form. In an embodiment, the overall yield of the two-step purification process is about 85%. In another embodiment, the purification is performed via a re-slurry in 2-butanone. In an embodiment, the yield of the purification process is about 85%. In an embodiment, the compound RY is RY'.

According to another aspect of the present invention, there is provided a compound RY or RY', and pharmaceutically acceptable salts thereof, prepared as described above.

According to another aspect of the present invention, there is provided a compound of formula F, wherein Ns is o-nitrophenylsulphonyl.

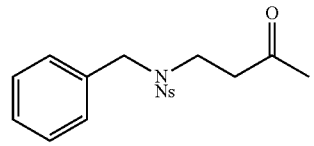

F

According to another aspect of the present invention, there is provided a process for preparing a compound of formula F. The process is as described above.

According to another aspect of the present invention, there is provided a process for preparing a compound of formula G as described above from the compound of formula F. The process is as described above. The present invention also provides the use of compound F in a process for preparing (R)-5-(2-(benzylamino)ethyl)-1-(6,8-difluorochroman-3-yl)-1H-imidazole-2(3H)-thione, or a pharmaceutically acceptable salt thereof, especially the hydrochloride salt.

According to another aspect of the present invention, there is provided a compound of formula G, wherein Ns is o-nitrophenylsulphonyl.

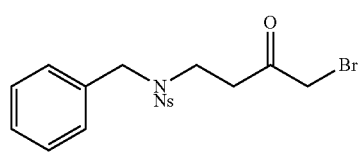

G

According to another aspect of the present invention, there is provided a process for preparing a compound of formula G. The process is as described above.

According to another aspect of the present invention, there is provided a process for preparing a compound of formula H as described above from the compound of formula G. The process is as described above. The present invention also provides the use of compound G in a process for preparing (R)-5-(2-(benzylamino)ethyl)-1-(6,8-difluorochroman-3-yl)-1H-imidazole-2(3H)-thione, or a pharmaceutically acceptable salt thereof, especially the hydrochloride salt.

According to another aspect of the present invention, there is provided a compound of formula H, wherein Ns is o-nitrophenylsulphonyl.

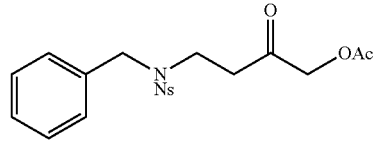

H

According to another aspect of the present invention, there is provided a process for preparing a compound of formula H. The process is as described above.

According to another aspect of the present invention, there is provided a process for preparing a compound of formula I as described above from the compound of formula H. The process is as described above. The present invention also provides the use of compound H in a process for preparing (R)-5-(2-(benzylamino)ethyl)-1-(6,8-difluorochroman-3-yl)-1H-imidazole-2(3H)-thione, or a pharmaceutically acceptable salt thereof, especially the hydrochloride salt.

According to another aspect of the present invention, there is provided a compound of formula I, wherein Ns is o-nitrophenylsulphonyl.

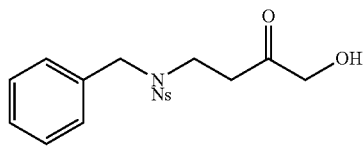

I

According to another aspect of the present invention, there is provided a process for preparing a compound of formula I. The process is as described above.

According to another aspect of the present invention, there is provided a process for preparing a compound of formula K as described above from the compound of formula I. The process is as described above. The present invention also provides the use of compound I in a process for preparing (R)-5-(2-(benzylamino)ethyl)-1-(6,8-difluorochroman-3-yl)-1H-imidazole-2(3H)-thione, or a pharmaceutically acceptable salt thereof, especially the hydrochloride salt.

According to another aspect of the present invention, there is provided a compound of formula K

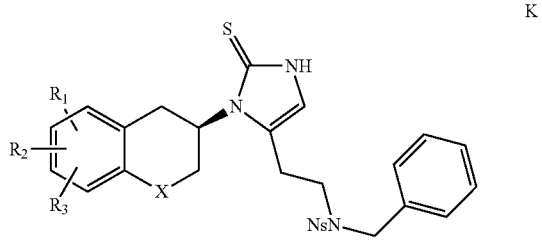

K where Ns is o-nitrophenylsulphonyl, $R_1$, $R_2$ and $R_3$ are the same or different and signify hydrogen, halogen, alkyl, nitro, amino, alkylcarbonylamino, alkylamino or dialkylamino group; and X signifies $CH_2$, oxygen atom or sulphur atom; wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyl, alkyloxy, halogen or nitro group; the term halogen means fluorine, chlorine, bromine or iodine; the term heteroaryl means heteroaromatic group.

In an embodiment, X is O.

In an embodiment, one of $R_1$, $R_2$ and $R_3$ is hydrogen, and the others are fluorine.

In an embodiment, compound K has the formula K'

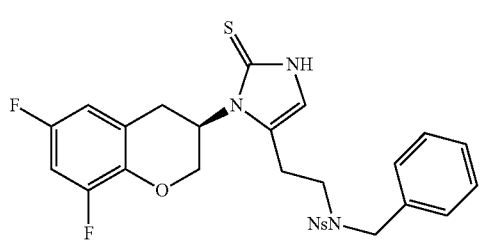

K'

According to another aspect of the present invention, there is provided a process for preparing a compound of formula K. The process is as described above.

According to another aspect of the present invention, there is provided a process for preparing a compound of formula RY as described above from the compound of formula K. The process is as described above. The present invention also provides the use of compound K in a process for preparing (R)-5-(2-(benzylamino)ethyl)-1-(6,8-difluorochroman-3-yl)-1H-imidazole-2(3H)-thione, or a pharmaceutically acceptable salt thereof, especially the hydrochloride salt.

According to another aspect of the present invention, there is provided a process for preparing a compound of formula K'. The process is as described above.

According to another aspect of the present invention, there is provided a process for preparing a compound of formula RY' as described above from the compound of formula K'. The process is as described above. The present invention also provides the use of compound K' in a process for preparing (R)-5-(2-(benzylamino)ethyl)-1-(6,8-difluorochroman-3-yl)-1H-imidazole-2(3H)-thione, or a pharmaceutically acceptable salt thereof, especially the hydrochloride salt.

According to another aspect of the present invention, there is provided a pharmaceutical composition comprising a compound RY or RY', or a pharmaceutically acceptable salt thereof, prepared as described above together with one or more pharmaceutically-acceptable excipients.

According to another aspect of the present invention, there is provided a composition comprising RY or RY', or a pharmaceutically acceptable salt thereof, preferably a therapeutically effective amount of compound RY or RY', or a pharmaceutically acceptable salt thereof, prepared as described above in combination with a pharmaceutically effective carrier and one or more of the compounds selected from the classes described below.

In particular, the compound RY or RY' as prepared by the present invention may be combined with one or more of the following classes of compounds: diuretics; beta-adrenergic antagonists; alpha2-adrenergic agonists; alpha1-adrenergic antagonists; dual beta- and alpha-adrenergic antagonists; calcium channel blockers; potassium channel activators; anti-arrhythmics; ACE inhibitors; AT1 receptor antagonists; renin inhibitors; lipid lowerers, vasopeptidase inhibitors; nitrates; endothelin antagonists; neutral endopeptidase inhibitors; anti-angiotensin vaccines; vasodilators; phosphodiesterase inhibitors; cardiac glycosides; serotonin antagonists; and CNS acting agents.

The most useful diuretics include:
(1) Loop diuretics, in particular, furosemide, bumetanide, ethacrynic acid, torasemide, azosemide, muzolimine, piretanide, tripamide.
(2) Thiazide diuretics, in particular, bendroflumethiazole, chlorothiazide, hydrochlorothiazide, hydroflumethiazide, methylclothiazide, polythiazide, trichlormethiazide.
(3) Thiazide-like diuretics, in particular, chlorthalidone, indapamide, metozalone, quinethazone.
(4) Potassium sparing diuretics, in particular, amiloride, triamterene.
(5) Aldosterone antagonists, in particular, spirolactone, canrenone, eplerenone.
(6) Combinations of the above described diuretics.

More than one of the aforementioned diuretics may be used.

The most useful beta-adrenergic antagonists include: timolol, metoprolol, atenolol, propranolol, bisoprolol, nebivolol. More than one of the aforementioned beta-adrenergic antagonists may be used.

The most useful alpha2-adrenergic agonists include: clonidine, guanabenz, guanfacine. More than one of the aforementioned alpha2-adrenergic agonists may be used.

The most useful alpha1-adrenergic antagonists include: prazosin, doxazosin, phentolamine. More than one of the aforementioned alpha1-adrenergic antagonists may be used.

The most useful dual beta- and alpha-adrenergic antagonists (other than those mentioned elsewhere in the specification) include: carvedilol, labetalol. More than one of the aforementioned dual beta- and alpha-adrenergic antagonists may be used.

Potassium channel activators include nicorandil.

The most useful calcium channel blockers include: amlodipine, bepridil, diltiazem, felodipine, isradipine, nicardipine, nifedipine, nimodipine, nisoldipine, verapamil. More than one of the aforementioned calcium channel blockers may be used.

Anti-arrhythmics other than those mentioned elsewhere in the specification include: sodium channel blockers such as quinidine, procainamide, disopyramide, lidocaine, mexiletine, tocainide, phenyloin, encainide, flecainide, moricizine, and propafenone; potassium channel blockers such as: amiodarone, bretylium, ibutilide, dofetilide, azimilide, clofilium, tedisamil, sematilide, sotalol; and esmolol, propranolol, metoprolol. More than one of the anti-arrhythmics mentioned in the specification may be used.

The most useful ACE inhibitors include: benzepril, captopril, enalapril, fosinopril, lisinopril, imidapril, moexipril, perindopril, quinapril, ramipril, trandolapril. More than one of the aforementioned ACE inhibitors may be used.

The most useful AT1 receptor antagonists include: candesartan, irbesartan, losartan, telmisartan, valsartan, eprosartan. More than one of the aforementioned AT1 receptor antagonists may be used.

Lipid lowerers include: statins such as atorvastatin, cerivastatin, fluvastatin, lovastatin, mevastatin, pitavastatin, pravastatin, rosuvastatin, simvastatin; bile acid sequestrants such as cholestyramine, colestipol and colesevelam; cholesterol absorption inhibitors such as ezetimibe; fibrates such as fenofibrate, gemfibrozil; niacin. More than one of the aforementioned lipid lowerers may be used.

The most useful nitrates include organic nitrates such as: amyl nitrite, nitroglycerin, isosorbide dinitrate, isosorbide-5-mononitrate, erythrityl tetranitrate. More than one of the aforementioned organic nitrates may be used.

Endothelin antagonists include: bosentan, sitaxsentan. More than one of the aforementioned endothelin antagonists may be used.

The most useful vasodilators (other than those mentioned elsewhere in the specification) include: hydralazine, minoxidil, sodium nitroprusside, diazoxide. More than one of the aforementioned vasodilators may be used.

The most useful phosphodiesterase inhibitors include: milrinone, inaminone. More than one of the aforementioned phosphodiesterase inhibitors may be used.

Cardiac glycosides include: allocar, corramedan, digitoxin, digoxin, lanoxin, purgoxin, cedilanid-D, crystodigin, lanoxicaps. More than one of the aforementioned cardiac glycosides may be used.

Serotonin antagonists include: clozapine, loxapine, olanzapine, risperidone, ziprasidone, ritanserin, ketanserin, amoxapine. More than one of the aforementioned serotonin antagonists may be used.

CNS acting agents other than those already mentioned elsewhere in this specification include imidazoline agonists such as moxonidine. The most useful CNS acting agent is methyldopa.

The most useful renin inhibitors include: aliskiren, enalkiren, ditekiren, terlakiren, remikiren, zankiren, ciprokiren. More than one of the aforementioned renin inhibitors may be used.

The most useful vasopeptidase inhibitors include: omapatrilat, sampatrilat, gemopatrilat. More than one of the aforementioned vasopeptidase inhibitors may be used.

Other pharmaceuticals used in treating heart failure may also be combined with the compound RY or RY' as prepared by the present invention. These include calcium sensitisers; HMG CoA reductase inhibitors; vasopressin antagonists; adenosine A1 receptor antagonists; atrial natriuretic peptide (ANP) agonists; chelating agents; corticotrophin-releasing factor receptor; glucagon-like peptide-1 agonists; sodium, potassium ATPase inhibitors; advanced glycosylation end-products (AGE) crosslink breakers; mixed neprilysin/endothelin-converting enzyme (NEP/ECE) inhibitors; nociceptin receptor (ORL-1) agonists (e.g. alprazolam); xanthine oxidase inhibitors; benzodiazepine agonists; cardiac myosin activators; chymase inhibitors; endothelial nitric oxide synthase (ENOS) transcription enhancers; neutral endopeptidase inhibitors such as thiorphan.

The invention also envisages the use of nepicastat with the classes of compounds described above.

For the preparation of pharmaceutical compositions of compound RY or RY', inert pharmaceutically acceptable carriers are admixed with the active compound. The pharmaceutically acceptable carriers may be either solid or liquid. Solid form preparations include powders, tablets, dispersible granules and capsules. A carrier can be one or more substances which may also act as diluents, flavouring agents, solubilizers, lubricants, suspending agents, binders or tablet disintegrating agents; it may also be an encapsulating material.

Preferably, the pharmaceutical preparation is in unit dosage form, e.g. packaged preparation, the package containing discrete quantities of preparation such as packeted tablets, capsules and powders in vials or ampoules.

The dosages may be varied depending on the requirement of the patient, the severity of the disease and the particular compound being employed. For convenience, the total daily dosage may be divided and administered in portions throughout the day. Suitable administration regimes for the compounds RY or RY' are thrice daily, twice daily, once daily, once every other day to once weekly. It is expected that once or twice per day administration will be most suitable. Determination of the proper dosage for a particular situation is within the skill of those in the medical art.

According to another aspect of the invention, there is provided a compound RY or RY' prepared as described above, for use as a medicament.

According to another aspect of the invention, there is provided the use of a compound RY or RY' prepared as described above, in the manufacture of a medicament for treating disorders where a reduction in the hydroxylation of dopamine to noradrenaline is of therapeutic benefit.

The compound RY or RY' may also be used in conjunction with one or more compounds selected from the following classes of compounds: diuretics; beta-adrenergic antagonists; alpha2-adrenergic agonists; alpha1-adrenergic antagonists; dual beta- and alpha-adrenergic antagonists; calcium channel blockers; potassium channel activators; anti-arrhythmics; ACE inhibitors; AT1 receptor antagonists; renin inhibitors; lipid lowerers, vasopeptidase inhibitors; nitrates; endothelin antagonists; neutral endopeptidase inhibitors; anti-angiotensin vaccines; vasodilators; phosphodiesterase inhibitors; cardiac glycosides; serotonin antagonists; CNS acting agents; calcium sensitisers; HMG CoA reductase inhibitors; vasopressin antagonists; adenosine A1 receptor antagonists; atrial natriuretic peptide (ANP) agonists; chelating agents; corticotrophin-releasing factor receptor; glucagon-like peptide-1 agonists; sodium, potassium ATPase inhibitors; advanced glycosylation end-products (AGE) crosslink breakers; mixed neprilysin/endothelin-converting enzyme (NEP/ECE) inhibitors; nociceptin receptor (ORL-1) agonists (e.g. alprazolam); xanthine oxidase inhibitors; benzodiazepine agonists; cardiac myosin activators; chymase inhibitors; endothelial nitric oxide synthase (ENOS) transcription enhancers; and neutral endopeptidase inhibitors such as thiorphan.

As used herein, the term treatment and variations such as 'treat' or 'treating' refer to any regime that can benefit a human or non-human animal. The treatment may be in respect of an existing condition or may be prophylactic (preventative treatment). Treatment may include curative, alleviation or prophylactic effects. Treatment with a compound RY or RY' in combination with one of the other classes of compounds includes simultaneous and sequential administration of the two or more drugs.

According to another aspect of the invention, there is provided the use of a compound RY or RY' prepared as described above, in the manufacture of a medicament for treating a subject afflicted by an anxiety disorder.

Anxiety disorders include but are not restricted to generalized anxiety disorders, social anxiety disorders, post-traumatic stress disorder, acute distress disorder, obsessive compulsive disorders, panic disorders such as panic attacks, and phobias such as agoraphobia, social phobias, specific phobias. Further, anxiety disorders treatable using compounds of the present invention may be found in on pages 429-484 of American Psychiatric Association: Diagnostic and Statistic Manual of Mental Disorders, 4th edition, Text Revision, Washington, D.C., American Psychiatric Association, 2000.

According to another aspect of the invention, there is provided the use of a compound RY or RY' prepared as described above, in the manufacture of a medicament for treating migraine.

According to another aspect of the invention, there is provided the use of a compound RY or RY' prepared as described above, in the manufacture of a medicament for treating a subject afflicted by a cardiovascular disorder.

According to another aspect of the invention, there is provided the use of a compound RY or RY' prepared as described above, in the manufacture of a medicament for treating hypertension, or chronic or congestive heart failure.

According to another aspect of the invention, there is provided the use of a compound RY or RY' prepared as described above, in the manufacture of a medicament for treating one or more of the following indications: angina, arrhythmias, and circulatory disorders such as Raynaud's phenomenon.

According to another aspect of the invention, there is provided the use of a compound RY or RY' prepared as described above, in the manufacture of a medicament for use in inhibiting dopamine-β-hydroxylase.

According to another aspect of the invention, there is provided a method of treating anxiety disorders comprising administering a therapeutically effective amount of a compound RY or RY' prepared as described above to a patient in need thereof.

According to another aspect of the invention, there is provided a method of treating migraine comprising administering a therapeutically effective amount of a compound RY or RY' prepared as described above to a patient in need thereof.

According to another aspect of the invention, there is provided a method of treating cardiovascular disorders comprising administering a therapeutically effective amount of a compound RY or RY' prepared as described above to a patient in need thereof.

According to another aspect of the invention, there is provided a method of treating hypertension comprising administering a therapeutically effective amount of a compound RY or RY' prepared as described above to a patient in need thereof.

According to another aspect of the invention, there is provided a method of treating chronic or congestive heart failure comprising administering a therapeutically effective amount of a compound of RY or RY' prepared as described above to a patient in need thereof.

According to another aspect of the invention, there is provided a method of treating one or more of the following indications: angina, arrhythmias, and circulatory disorders such as Raynaud's phenomenon, comprising administering a therapeutically effective amount of a compound RY or RY' prepared as described above to a patient in need thereof.

The above-described methods of treatment may further comprise simultaneous or sequential administration of a drug from one of the following classes of compounds: diuretics; beta-adrenergic antagonists; alpha2-adrenergic agonists; alpha1-adrenergic antagonists; dual beta- and alpha-adrenergic antagonists; calcium channel blockers; potassium channel activators; anti-arrhythmics; ACE inhibitors; AT1 receptor antagonists; renin inhibitors; lipid lowerers, vasopeptidase inhibitors; nitrates; endothelin antagonists; neutral endopeptidase inhibitors; anti-angiotensin vaccines; vasodilators; phosphodiesterase inhibitors; cardiac glycosides; serotonin antagonists; CNS acting agents; calcium sensitisers; HMG CoA reductase inhibitors; vasopressin antagonists; adenosine A1 receptor antagonists; atrial natriuretic peptide (ANP) agonists; chelating agents; corticotrophin-releasing factor receptor; glucagon-like peptide-1 agonists; sodium, potassium ATPase inhibitors; advanced glycosylation end-products (AGE) crosslink breakers; mixed neprilysin/endothelin-converting enzyme (NEP/ECE) inhibitors; nociceptin receptor (ORL-1) agonists (e.g. alprazolam); xanthine oxidase inhibitors; benzodiazepine agonists; cardiac myosin activators; chymase inhibitors; endothelial nitric oxide synthase (ENOS) transcription enhancers; and neutral endopeptidase inhibitors such as thiorphan.

EXAMPLES

The following non-limiting examples describe embodiments of the present invention.

NMR spectra were recorded at 20° C., on a Bruker Avance DPX 400 MHz, or a 600 MHz Avance III spectrometer with solvent used as internal standard. Data are reported in the following order: approximate chemical shift (ppm), number of protons, multiplicity (br, broad; d d, doublet of doublet; d t, doublet of triplet; m, multiplet; m d, multiplet of doublet; m t, multiplet of triplet; s, singlet) and coupling constant (Hz).

Example 1

N-benzyl-4-hydroxy-3-oxobutanamide (Compound C)

To a solution of N-benzyl-3-oxobutanamide (compound A 50 g, 261 mmol) in dichloromethane (350 ml) was added bromine (14.82 ml, 288 mmol) at 0-5° C., then stirred at 20-25° C. for 3 hours (bromine colour disappeared). Water (300 ml) was added to the mixture with stirring, stirred for 10 min. Organic phase was separated, washed with sodium bicarbonate solution, dried, evaporated to dryness (compound B). The solid residue (compound B) dissolved in methanol (900 ml), added potassium formate (44.0 g, 523 mmol) and the mixture was heated under reflux for 2 hours. Methanol was removed on a rotavap, the residue was taken up into ethyl acetate (EA) (500 ml) under reflux, filtered hot, the filter cake washed with warm EA (100 ml). The combined filtrate was cooled to 5-10° C., aged for 1.5 hours. The precipitate was collected, washed with cold EA (50 ml), dried to give 25 g (46.1%) of crude product, light beige. Re-crystallised from water (300 ml), with active carbon (1 g). Filtered hot on celite, cooled in ice, aged for 1 hour, crystals collected, washed with cold water (20 ml), dried on air overnight to give N-benzyl-4-hydroxy-3-oxobutanamide (21 g, 101 mmol, 38.8% yield).

$^1$H NMR (600 MHz, 20° C., DMSO) δ: 13.92 (0.1H, s br), 8.53 (1H, t, J=5.5 Hz), 7.32 (2H, m t, J=7.5 Hz), 7.27 (2H, m d, J=8.0 Hz), 7.24 (1H, m t, J=7.0 Hz), 5.32 (0.1H, s br), 5.25 (1H, t, J=6.1 Hz), 4.32 (0.2H, d, J=6.1 Hz), 4.28 (1.8H, d, J=5.9 Hz), 4.17 (1.8H, d, J=6.1 Hz), 3.89 (0.2H, s br), 3.37 (1.8H, s); $^{13}$C NMR (100 MHz, 20° C., DMSO) δ: 205.6, 166, 139.2, 128.3, 127.3, 126.9, 88.4, 67.8, 60.5, 46.6, 42.2, 41.6.

Example 2

N-benzyl-4-bromo-3-oxobutanamide (Compound B)

To a solution of N-benzyl-3-oxobutanamide (compound A 100 g, 522.9 mmol) in dichloromethane (500 ml) at 0-5° C. was added dropwise a solution of bromine (25.55 ml, 575.2 mmol) over 6 h. The reaction mixture was warmed up to 20-25° C. and stirred for 2 hours (bromine colour disappeared). An aqueous solution (600 mL) of sodium bicarbonate (65.9 g, 784.44 mmol) was added to the mixture. The organic layer was separated, washed with brine (200 mL), and then evaporated to dryness to give N-benzyl-4-bromo-3-oxobutanamide (114.25 g, quantitative) and was used in the next step without further purification.

$^1$H NMR, 600 MHz, 20° C., CDCl$_3$) δ: 13.7 (0.3H, s br), 7.38-7.33 (2H, m), 7.33-7.27 (3H, m), 6.85 (0.7H, s br), 5.61 (0.3H, s br), 5.14 (0.3H, s), 4.50, 4.48 (2H, 2 d, J=5.9, J=5.7 Hz), 4.06 (1.4H, s), 3.48 (0.6; H, s), 3.68 (1.4H, s); $^{13}$C NMR (100 MHz, 20° C., CDCl$_3$) δ: 197.4, 170.7, 168.8, 164.5, 137.5, 137.4, 128.8, 128.8, 127.8, 127.8, 127.8, 127.7, 92.3, 46.6, 43.8, 43.2, 34.5, 29.4.

Example 3

N-benzyl-4-hydroxy-3-oxobutanamide (Compound C)

N-benzyl-4-bromo-3-oxobutanamide (compound B 50 g, 185.1 mmol) was dissolved in methanol (400 ml), and potassium formate (31.14 g, 370.2 mmol) was added. The resulting mixture was heated under reflux for 2 hours. Methanol was removed by distillation under reduced pressure; the residue was taken up into ethyl acetate (250 ml) under reflux, filtered hot, the filter cake washed with warm ethyl acetate (100 ml). The combined filtrate was cooled to −10° C., aged for 1.5 hours. The precipitate was collected, washed twice with cold ethyl acetate (2×25 ml), dried to give N-benzyl-4-hydroxy-3-oxobutanamide (18.2 g, 101 mmol, 38.8% yield).

$^1$H NMR (600 MHz, 20° C., DMSO) δ: 13.92 (0.1H, s br), 8.53 (1H, t, J=5.5 Hz), 7.32 (2H, m t, J=7.5 Hz), 7.27 (2H, m d, J=8.0 Hz), 7.24 (1H, m t, J=7.0 Hz), 5.32 (0.1H, s br), 5.25 (1H, t, J=6.1 Hz), 4.32 (0.2H, d, J=6.1 Hz), 4.28 (1.8H, d, J=5.9 Hz), 4.17 (1.8H, d, J=6.1 Hz), 3.89 (0.2H, s br), 3.37 (1.8H, s); $^{13}$C NMR (100 MHz, 20° C., DMSO) δ: 205.6, 166, 139.2, 128.3, 127.3, 126.9, 88.4, 67.8, 60.5, 46.6, 42.2, 41.6.

Example 4

(R)—N-benzyl-2-(3-(6,8-difluorochroman-3-yl)-2-thioxo-2,3-dihydro-1H-imidazol-4-yl)acetamide (Compound D')

To a mixture of (R)-6,8-difluorochroman-3-amine(2R, 3R)-2,3-dihydroxysuccinate (compound JT', 15 g, 44.7 mmol) and potassium thiocyanate (5.22 g, 53.7 mmol) in 2-propanol (150 ml) was added acetic acid (38.4 ml, 671 mmol) followed by N-benzyl-4-hydroxy-3-oxobutanamide (compound C, 11.13 g, 53.7 mmol) in 5 portions during 1 hours. The mixture was heated with stirring at 80° C. for 2 hours. More N-benzyl-4-hydroxy-3-oxobutanamide (1.854 g, 8.95 mmol) and potassium thiocyanate (0.870 g, 8.95 mmol) added, stirred for 1 hour. More N-benzyl-4-hydroxy-3-oxobutanamide (1.854 g, 8.95 mmol) and potassium thiocyanate (0.870 g, 8.95 mmol) added, stirred for 1 hour (in total N-benzyl-4-hydroxy-3-oxobutanamide (14.83 g, 71.6 mmol) and potassium thiocyanate (6.96 g, 71.6 mmol)), purified by HPLC at 210 nm (Kromasil 100 5C4 250×4.6 column, 0.1% TFA-ACN 50:50, 1 ml/min) with less than 1.5% compound JT'. Diluted with water (110 ml) at approx 50° C., cooled to 5° C. and aged for 1 hour. Precipitate was collected, washed with water. Wet filter cake was re-slurried in water (300 ml), solution of sodium bicarbonate (4.13 g, 49.2 mmol) in water (100 ml) was added in portions, the mixture was stirred for 15 min, filtered, washed with water (wet weight 21 g), dried on air to give (R)—N-benzyl-2-(3-(6,8-difluorochroman-3-yl)-2-thioxo-2,3-dihydro-1H-imidazol-4-yl)acetamide (12.2 g, 29.4 mmol, 65.6% yield).

$^1$H NMR (600 MHz, 20° C., DMSO) δ: 12.22 (1H, s br), 8.56 (1H, t, J=5.9 Hz), 7.26-7.10 (6H, m), 6.90 (1H, d br, J=8.8 Hz), 6.81 (1H, s), 5.27 (1H, s br), 4.60 (2H, br), 4.32 (1H, m d, J=10.3 Hz), 4.25 (2H, m), 3.63 (2H, d, J=1.7 Hz), 2.90 (1H, dd, J=5.2, 16.0 Hz); $^{13}$C NMR (100 MHz, 20° C., DMSO) δ: 168.3, 160.4, 155.1 (d d, J=11.2, 238.5 Hz), 150.5 (d d, J=12.9, 246.5 Hz), 139.1, 138.3 (d d, J=3.2, 11.5 Hz), 128.3, 127.4, 126.9, 126, 124.8 (d d, J=2.2, 9.4 Hz), 114.3, 111.2 (d d, J=3.5, 23.0 Hz), 102.6 (d d, J=22.1, 27.5 Hz), 64.5, 49.6, 42.5, 31.1, 26.5

Example 5

(R)-5-(2-(benzylamino)ethyl)-1-(6,8-difluorochroman-3-yl)-1H-imidazole-2(3H)-thione (Compound RY')

To a solution of (R)—N-benzyl-2-(3-(6,8-difluorochroman-3-yl)-2-thioxo-2,3-dihydro-1H-imidazol-4-yl)acetamide (1 g, 2.407 mmol) in tetrahydrofuran (10 ml) was added sodium borohydride (0.455 g, 12.03 mmol) followed by solution of boron trifluoride etherate (1.525 ml, 12.03 mmol) in tetrahydrofuran (5 ml) with ice cooling dropwise during 10 min, allowed to warm up naturally and stirred at 20-25° C. under Ar. After 7 hours still 7.5% of starting material (SM), the reaction was left overnight with stirring. Quenched with 1N hydrochloric acid (5 ml, 5.00 mmol) with ice-cooling (first drops caused intensive foaming), pH to 1 with 6N hydrochloric acid (2 ml, 12.00 mmol), the mixture refluxed for 30 min. Diluted with water, THF removed on a rotavap (crystallisation occurred), the residue aged for 1 hour at RT. Precipitate collected, washed with water. Dried at 50° C. in vacuum to give 1.13 g of solid. Dissolved in Methanol (15.00 ml) and water (2.3 ml), heated to reflux, 1N sodium hydroxide (2.65 ml, 2.65 mmol) added (pH 8-9). No immediate crystallisation, crystallised at approx 50° C. Cooled to 20-25° C., aged for 30 min, precipitate collected, washed with MeOH, dried in vacuum at 50° C. to give (R)-5-(2-(benzylamino)ethyl)-1-(6,8-difluorochroman-3-yl)-1H-imidazole-2(3H)-thione (0.73 g, 1.818 mmol, 76% yield).

$^1$H NMR (400 MHz, DMSO, 20° C.) δ: 12.05 (1H, br, NH), 7.31-7.21 (4H, m), 7.21-7.12 (2H, m), 6.89 (1H, d, br, J=9.0 Hz), 6.74 (1H, s), 5.19 (1H, s, br), 4.82 (1H, s, br), 4.41 (1H, s, br), 4.28 (1H, m, J=3.5, 11.0 Hz), 3.68 (2H, s), 2.87 (1H, dd, J=6.0, 16.5 Hz), 2.77-2.57 (4H, m); $^{13}$C NMR (100 MHz, DMSO, 20° C.) δ: 160.3, 155.1 (dd, J=11.0, 238.0 Hz), 150.5 (dd, J=13.5, 246.5 Hz), 140.8, 138.4 (dd, J=3.5, 11.5 Hz), 129.8, 128.1, 127.9, 126.5, 124.8 (dd, J=2.5, 9.5 Hz), 112.4, 111.2 (dd, J=3.5, 22.5 Hz), 102.7 (dd, J=22.0, 27.5), 64.8, 52.7, 48.9, 47.6, 27.0, 24.8.

Example 6

(R)-5-(2-(benzylamino)ethyl)-1-(6,8-difluorochroman-3-yl)-1H-imidazole-2(3H)-thione (Compound RY')

To a solution of (R)—N-benzyl-2-(3-(6,8-difluorochroman-3-yl)-2-thioxo-2,3-dihydro-1H-imidazol-4-yl)acetamide (16.62 g, 40 mmol) in tetrahydrofuran (133 ml) was added sodium borohydride (3.78 g, 100 mmol). The suspension was then cooled to 0° C. and a solution of boron trifluoride tetrahydrofuran (14.56 ml, 132 mmol) in tetrahydrofuran (85 ml). The mixture was warmed up to room temperature (20-25° C.) and stirred for 24 hours. After cooling to 0° C., 1N hydrochloric acid (64 ml, 64 mmol), pH to 1 with 6N hydrochloric acid (17.7 ml, 108 mmol), and the mixture was refluxed for 30 min. Tetrahydrofuran was removed under reduced pressure. The precipitate was collected, washed with water (50 mL). The wet solid was suspended in a mixture of methanol (250 ml) and water (38 ml). The suspension was heated to reflux until complete dissolution; 1N sodium hydroxide (45 ml, 48 mmol) was added (pH 8-9). The crystallization occurred at approx 50° C. The suspension was cooled to 15° C., aged for 3 hours. The precipitate was collected, washed with methanol (33 mL), dried in vacuum at 50° C. to give (R)-5-(2-(benzylamino)ethyl)-1-(6,8-difluorochroman-3-yl)-1H-imidazole-2(3H)-thione (12.5 g, 30.01 mmol, 76% yield).

$^1$H NMR (400 MHz, DMSO, 20° C.) δ: 12.05 (1H, br, NH), 7.31-7.21 (4H, m), 7.21-7.12 (2H, m), 6.89 (1H, d, br, J=9.0 Hz), 6.74 (1H, s), 5.19 (1H, s, br), 4.82 (1H, s, br), 4.41 (1H, s, br), 4.28 (1H, m, J=3.5, 11.0 Hz), 3.68 (2H, s), 2.87 (1H, dd, J=6.0, 16.5 Hz), 2.77-2.57 (4H, m); $^{13}$C NMR (100 MHz, DMSO, 20° C.) δ: 160.3, 155.1 (dd, J=11.0, 238.0 Hz), 150.5 (dd, J=13.5, 246.5 Hz), 140.8, 138.4 (dd, J=3.5, 11.5 Hz), 129.8, 128.1, 127.9, 126.5, 124.8 (dd, J=2.5, 9.5 Hz), 112.4, 111.2 (dd, J=3.5, 22.5 Hz), 102.7 (dd, J=22.0, 27.5), 64.8, 52.7, 48.9, 47.6, 27.0, 24.8.

Example 7

N-benzyl-2-nitro-N-(3-oxobutyl)benzenesulfonamide (Compound F)

To a solution of benzylamine (10.92 ml, 100 mmol) in dichloromethane (DCM) (150 ml) was added triethylamine (13.67 ml, 100 mmol) followed by a solution of 2-nitrobenzene-1-sulfonyl chloride (22.16 g, 100 mmol) in DCM (70 ml) at 5-10° C. with stirring. The mixture was stirred for 1 hour (complete by HPLC), stirring continued for 1 hour, washed with water, brine, most of DCM removed on a rotavap, Ethyl acetate (150 ml) was added, another 25-30 ml distilled off under reduced pressure. To the resulting solution potassium tert-butoxide (0.561 g, 5.00 mmol) was added followed by methyl vinyl ketone (9.07 ml, 110 mmol) with stirring in one portion at 20-25° C. The mixture was stirred for 1 hour at 20-25° C., diluted with heptane (70 ml), washed with brine+1N HCl (5 ml), organic phase was dried (MgSO$_4$), evaporated to approx 100 ml, seeded with crystals of compound F (crystallisation started), cooled to 0-5° C., diluted slowly with heptane to approx 200 ml. The mixture was aged in ice for 1 hour, crystals collected, washed with heptane, dried on air to give N-benzyl-2-nitro-N-(3-oxobutyl)benzenesulfonamide (31.4 g, 87 mmol, 87% yield).

$^1$HNMR (600 MHz, 20° C., CDCl$_3$) δ: 7.98 (1H, m), 7.71 (1H, m), 7.68-7.64 (2H, m), 7.35-7.27 (5H, m), 4.51 (2H, s), 3.50 (2H, m), 2.55 (2H, m), 1.97 (3H, s); $^{13}$C NMR (100 MHz, 20° C., CDCl$_3$) δ: 206.4, 148, 135.7, 133.6, 132.9, 131.8, 130.8, 128.8, 128.3, 128.1, 124.2, 52.8, 42.6, 42.5, 30.

Example 8

N-benzyl-2-nitro-N-(3-oxobutyl)benzenesulfonamide (Compound F)

To a solution of benzylamine (1 ml, 9.16 mmol) in ethyl acetate (10 ml) was added triethylamine (1.252 ml, 9.16 mmol) followed 2-nitrobenzene-1-sulfonyl chloride (2.03 g, 9.16 mmol) at 5-10° C. with stirring. The mixture was stirred for 1 hour (complete by HPLC), stirring continued for 1 hour. The reaction mixture was quenched with water. The organic layer was separated, washed with brine, dried, and concentrated under reduced pressure. The residue was dissolved in ethyl acetate (8 ml) and to the resulting solution potassium tert-butoxide (0.051 g, 0.458 mmol) was added followed by methyl vinyl ketone (0.755 ml, 9.16 mmol) with stirring in one portion at 20-25° C. The mixture was stirred for 2 hours at 20-25° C., quenched with brine. The organic phase was separated and the aqueous layer was back extracted with ethyl acetate (5 mL). The combined organic layers were washed with 0.6N HCl (10 mL), concentrated to 3 volumes. The solution was diluted with isopropanol (20 mL), concentrated under reduced pressure until a precipitate appeared. The resulting slurry was then stirred at 20° C. for 4 hours, filtered. The collected solid was then washed with 2-propanol (2×40 mL), dried to give N-benzyl-2-nitro-N-(3-oxobutyl)benzenesulfonamide (2.5 g, 6.87 mmol, 75% yield).

$^1$H NMR (600 MHz, 20° C., CDCl$_3$) δ: 7.98 (1H, m), 7.71 (1H, m), 7.68-7.64 (2H, m), 7.35-7.27 (5H, m), 4.51 (2H, s), 3.50 (2H, m), 2.55 (2H, m), 1.97 (3H, s); $^{13}$C NMR (100 MHz, 20° C., CDCl$_3$) δ: 206.4, 148, 135.7, 133.6, 132.9, 131.8, 130.8, 128.8, 128.3, 128.1, 124.2, 52.8, 42.6, 42.5, 30.

Example 9

N-benzyl-N-(4-bromo-3-oxobutyl)-2-nitrobenzenesulfonamide (Compound G)

To a solution of N-benzyl-2-nitro-N-(3-oxobutyl)benzenesulfonamide (compound F, 30 g, 83 mmol) in methanol (300 ml) was added bromine (4.69 ml, 91 mmol) in one portion at 20-25° C. Stirred for 20 hours (no bromine colour), water (20 ml) added, heated to reflux for 30 min, diluted with MeOH (100 ml). The solution was cooled to 30° C. with stirring, seeded with compound G, stirred at 25-30° C. for 5 min (crystallisation occurred), cooled to 15° C., aged for 1 hour. Crystals collected, washed with 2×15 ml of MeOH (20-25° C.), dried on air to give N-benzyl-N-(4-bromo-3-oxobutyl)-2-nitrobenzenesulfonamide (19.4 g, 44.0 mmol, 53.1% yield).

$^1$H NMR (400 MHz, 20° C., CDCl$_3$) δ: 8.0 (1H, m), 7.73 (1H, m), 7.70-7.66 (2H, m), 7.38-7.27 (5H, m), 4.52 (2H, s), 3.69 (2H, s), 3.55 (2H, m t, J=7.2 Hz), 2.75 (2H, m t, J=7.1 Hz); $^{13}$C NMR (100 MHz, 20° C., CDCl$_3$) δ: 199.8, 148, 135.5, 133.8, 132.8, 131.8, 131, 128.9, 128.4, 128.3, 124.3, 53, 42.8, 39.1, 34.1.

Example 10

N-benzyl-N-(4-hydroxy-3-oxobutyl)-2-nitrobenzenesulfonamide (Compound I)

A mixture of N-benzyl-N-(4-bromo-3-oxobutyl)-2-nitrobenzenesulfonamide (16 g, 36.3 mmol) and potassium acetate (8.90 g, 91 mmol) in acetic acid (130 ml) was heated to 110-115° C. (slow reflux visible) and stirred for 1 hour (complete by HPLC). Cooled, acetic acid (80 ml) removed under reduced pressure, the residue distributed between DCM (120 ml) and water (120 ml). The organic phase was washed with water, evaporated to half of the volume, diluted with 2-propanol (65.0 ml), the rest of DCM removed. Water (18.20 ml) was added followed by concentrated hydrochloric acid (2.102 ml, 25.4 mmol), residual DCM was distilled off at atmospheric pressure until head temperature reached 77° C., then stirred under reflux for 3 hours. Diluted with water (65 ml), 2-propanol removed at 60° C./180 mbar, to the biphasic residue EA (80 ml) was added followed by sodium bicarbonate with stirring until evolution of gas stopped. The organic phase was dried (MgSO$_4$), evaporated to dryness to give N-benzyl-N-(4-hydroxy-3-oxobutyl)-2-nitrobenzenesulfonamide (13.2 g, 34.9 mmol, 96% yield).

$^1$H NMR (400 MHz, 20° C., CDCl$_3$) δ: 8.0 (1H, m), 7.78-7.64 (3H, m), 7.39-7.27 (5H, m), 4.51 (2H, s), 4.03 (2H, d br, J=4.0 Hz), 3.59 (2H, m t, J=7.2 Hz), 2.83 (1H, t br, J=4.0 Hz), 2.51 (2H, m t, J=7.0 Hz); $^{13}$C NMR (100 MHz, 20° C., CDCl$_3$) δ: 207.3, 148, 135.4, 133.8, 132.7, 131.8, 131, 128.9, 128.3, 128.3, 124.3, 68.1, 53, 42.4, 37.7.

Example 11

N-benzyl-N-(4-hydroxy-3-oxobutyl)-2-nitrobenzenesulfonamide (Compound I)

A suspension of N-benzyl-N-(4-bromo-3-oxobutyl)-2-nitrobenzenesulfonamide (Compound G, 200 mg, 0.453 mmol), formic acid (0.100 ml, 2.65 mmol) and potassium formate (76 mg, 0.906 mmol) in methanol (2 ml) was heated to reflux for 2 hours. The reaction mixture was then cooled to room temperature and then filtered to remove inorganic salt. The filtrate was then concentrated under reduced pressure, then diluted in ethyl acetate. The resulting slurry was then filtered and the solid was washed with ethyl acetate. The resulting combined filtrates were concentrated under reduced pressure. N-benzyl-N-(4-hydroxy-3-oxobutyl)-2-nitrobenzenesulfonamide (Compound I, 169 mg, 0.447 mmol, 99% yield) was obtained as a pale yellow oil.

$^1$H NMR (400 MHz, 20° C., CDCl$_3$) δ: 8.0 (1H, m), 7.78-7.64 (3H, m), 7.39-7.27 (5H, m), 4.51 (2H, s), 4.03 (2H, d br, J=4.0 Hz), 3.59 (2H, m t, J=7.2 Hz), 2.83 (1H, t br, J=4.0 Hz), 2.51 (2H, m t, J=7.0 Hz); $^{13}$C NMR (100 MHz, 20° C., CDCl$_3$) δ: 207.3, 148, 135.4, 133.8, 132.7, 131.8, 131, 128.9, 128.3, 128.3, 124.3, 68.1, 53, 42.4, 37.7.

Example 12

(R)—N-benzyl-N-(2-(3-(6,8-difluorochroman-3-yl)-2-thioxo-2,3-dihydro-1H-imidazol-4-yl)ethyl)-2-nitrobenzenesulfonamide (Compound K')

To a mixture of (R)-6,8-difluorochroman-3-amine(2R, 3R)-2,3-dihydroxysuccinate (compound JT', 1.7 g, 5.07 mmol), N-benzyl-N-(4-hydroxy-3-oxobutyl)-2-nitrobenzenesulfonamide (compound I, 2.303 g, 6.08 mmol) in acetic acid (12.5 ml) was added potassium thiocyanate (0.591 g, 6.08 mmol) in one portion. The mixture was heated with stirring at 100° C. for 3 hours under HPLC control, cooled to 20° C., diluted with 2-propanol (55 ml), cooled to 0° C., aged for 1 hour. The precipitate collected, washed with cold 2-propanol (55 ml), dried to give 12.54 g. The solid was suspended in a mixture of water (38 ml) and ethanol (EtOH) (19 ml), solid sodium bicarbonate (2.255 g, 26.8 mmol) was added in portions with stirring at 20-25° C., stirred for 30 min. Solid collected, washed with water, dried to give (R)—N-benzyl-N-(2-(3-(6,8-difluorochroman-3-yl)-2-thioxo-2,3-dihydro-1H-imidazol-4-yl)ethyl)-2-nitrobenzenesulfonamide (compound K', 8.4 g, 14.32 mmol, 64.0% yield).

$^1$H NMR (600 MHz, 20° C., DMSO) δ: 12.16 (1H, s br), 8.04 (1H, dd, J=1.2, 8.0 Hz), 8.0 (1H, dd, J=1.3, 8.0 Hz), 7.89 (1H, d t, J=1.3, 7.6 Hz), 7.81 (1H, d t, J=1.3, 7.8 Hz), 7.28-7.14 (6H, m), 6.88 (1H, d br, J=8.5 Hz), 6.68 (1H, s), 5.03 (1H, br), 4.56 (2H, s), 4.56 (1H, br), 4.18 (1H, m d, J=10.5 Hz), 4.18 (1H, br), 3.41 (2H, m), 2.76 (1H, dd, J=5.5, 16.5 Hz), 2.61 (2H, m); $^{13}$C NMR (150 MHz, 20° C., DMSO) δ: 160.8, 155.1 (d d, J=11.2, 238.0 Hz), 150.5 (d d, J=13.3, 246.7 Hz), 147.5, 138.4 (d d, J=3.0, 11.5 Hz), 135.9, 134.7, 132.6, 131.7, 129.9, 128.6, 128.1, 127.9, 127, 124.5 (d d, J=2.5, 10.0 Hz), 124.4, 113, 111.1 (d d, J=3.5, 22.8 Hz), 102.7 (d d, J=22.0, 27.0 Hz), 64.5, 50.8, 48.8, 46.3, 26.9, 23.4.

Example 13

(R)-5-(2-(benzylamino)ethyl)-1-(6,8-difluorochroman-3-yl)-1H-imidazole-2(3H)-thione (Compound RY' Crude)

To a solution of (R)—N-benzyl-N-(2-(3-(6,8-difluorochroman-3-yl)-2-thioxo-2,3-dihydro-1H-imidazol-4-yl)ethyl)-2-nitrobenzenesulfonamide (compound K', 8 g, 13.64 mmol) and 2-mercaptoacetic acid (2.84 ml, 40.9 mmol) in dimethylformamide (DMF) (80 ml) was added 10N potassium hydroxide (10.23 ml, 102 mmol) in one portion with water cooling and the mixture was stirred at 20-25° C. under HPLC control for 3 hours. Methanol-water 1:1 (160 ml) was slowly added with stirring, the mixture was stirred for 2 hours at 20-25° C. Precipitate was collected, washed with MeOH-water 1:1 (80 ml), dried to give (R)-5-(2-(benzylamino) ethyl)-1-(6,8-difluorochroman-3-yl)-1H-imidazole-2(3H)-thione (4.96 g, 12.35 mmol, 91% yield).

$^1$H NMR (400 MHz, DMSO, 20° C.) δ: 12.05 (1H, br, NH), 7.31-7.21 (4H, m), 7.21-7.12 (2H, m), 6.89 (1H, d, br, J=9.0 Hz), 6.74 (1H, s), 5.19 (1H, s, br), 4.82 (1H, s, br), 4.41 (1H, s, br), 4.28 (1H, m, J=3.5, 11.0 Hz), 3.68 (2H, s), 2.87 (1H, dd, J=6.0, 16.5 Hz), 2.77-2.57 (4H, m); $^{13}$C NMR (100 MHz, DMSO, 20° C.) δ: 160.3, 155.1 (dd, J=11.0, 238.0 Hz), 150.5 (dd, J=13.5, 246.5 Hz), 140.8, 138.4 (dd, J=3.5, 11.5 Hz), 129.8, 128.1, 127.9, 126.5, 124.8 (dd, J=2.5, 9.5 Hz), 112.4, 111.2 (dd, J=3.5, 22.5 Hz), 102.7 (dd, J=22.0, 27.5), 64.8, 52.7, 48.9, 47.6, 27.0, 24.8.

Example 14

(R)-5-(2-(benzylamino)ethyl)-1-(6,8-difluorochroman-3-yl)-1H-imidazole-2(3H)-thione (Compound RY' Crude)

To a solution of potassium hydroxide (5M aqueous solution, 52.5 ml, 263 mmol) in water at 10° C. was added dropwise 2-mercaptoacetic acid (8.30 ml, 119 mmol). The resulting solution was stirred at room temperature for 10 minutes and a solution of (R)—N-benzyl-N-(2-(3-(6,8-difluorochroman-3-yl)-2-thioxo-2,3-dihydro-1H-imidazol-4-yl)ethyl)-2-nitrobenzenesulfonamide (28 g, 47.7 mmol) in DMSO (150 ml) was added dropwise over 20 minutes. During the addition of KOH, an exothermic event was observed. The resulting slurry was stirred at 40° C. under HPLC control for 3 h. The reaction was then cooled to 20° C. and methanol (105 ml) was added followed by water (45 ml). The resulting slurry was aged for 30 minutes at 20° C. and then filtered. The beige solid was successively washed with water/MeOH (9:1) (100 ml), water (200 ml) and finally methyl tert-butyl ether (MTBE) (50 ml), dried to give (R)-5-(2-(benzylamino)ethyl)-1-(6,8-difluorochroman-3-yl)-1H-imidazole-2(3H)-thione (compound RY', 18.3 g, 12.35 mmol, 96% yield).

Example 15

(R)-5-(2-(benzylamino)ethyl)-1-(6,8-difluorochroman-3-yl)-1H-imidazole-2(3H)-thione hydrochloride (HCl Salt of Compound RY' Purified)

To a suspension of (R)-5-(2-(benzylamino)ethyl)-1-(6,8-difluorochroman-3-yl)-1H-imidazole-2(3H)-thione (2 g, 4.98 mmol) in methanol (MeOH) (30 ml) was added 1.5M hydrochloric acid (3.32 ml, 4.98 mmol) in MeOH to give a clear solution. To the solution Toluene (30.0 ml) was added, MeOH (30 ml) was removed on a rotavap followed by addition of toluene (20 ml). The mixture was aged with stirring for 1 hours at 0-5° C., the precipitate collected, washed with toluene (10 ml), dried in vacuum at 50° C. to give 2.05 g (94%) of purified (R)-5-(2-(benzylamino)ethyl)-1-(6,8-difluorochroman-3-yl)-1H-imidazole-2(3H)-thione hydrochloride.
$^1$H NMR (400 MHz, DMSO, 20° C.) δ: 12.32 (1H, br), 9.52 (2H, s, br), 7.57 (2H, m, J=7.8 Hz), 7.41 (3H, m), 7.16 (1H, m), 6.94 (1H, d, br, J=9 Hz), 6.91 (1H, d, J=2.5 Hz), 5.18 (1H, s, br), 4.84 (1H, s, br), 4.42 (1H, s, br), 4.36 (1H, m, J=10.5), 4.16 (2H, br), 3.08 (4H, m), 2.93 (1H, dd, J=5.5 and 16.5 Hz); $^{13}$C NMR (100 MHz, DMSO, 20° C.) δ: 160.0, 155.1 (dd, J=11.5 and 239.0 Hz), 150.5 (dd, J=13.5 and 246.5 Hz), 138.4 (dd, J=3.0 and 11.5 Hz), 132.1, 130.0, 128.9, 128.7, 126.3, 124.6 (dd, J=2.0 and 9.0 Hz), 113.7, 111.2 (dd, J=3.5 and 22.5 Hz), 102.7 (dd, J=22.0 and 27.0 Hz), 64.6, 49.8, 48.9, 44.8, 27.0, 21.0.

Example 16

(R)-5-(2-(benzylamino)ethyl)-1-(6,8-difluorochroman-3-yl)-1H-imidazole-2(3H)-thione (Compound RY' Purified)

(R)-5-(2-(benzylamino)ethyl)-1-(6,8-difluorochroman-3-yl)-1H-imidazole-2(3H)-thione hydrochloride (8 g, 18.27 mmol) was dissolved in methanol (120 ml) at 40-45° C., diluted with water (18.00 ml), crystallisation occurred. The precipitate was dissolved with heating to 67-68° C. and stirring. To the solution 1N sodium hydroxide (19.18 ml, 19.18 mmol) was added dropwise during 1 hour via a syringe pump. The mixture was aged for 30 min at 67° C., cooled to 20° C. during 1 hour, aged at 20° C. for 30 min. Crystals were collected, washed with MeOH-water 1:1 (36 ml), dried to give (R)-5-(2-(benzylamino)ethyl)-1-(6,8-difluorochroman-3-yl)-1H-imidazole-2(3H)-thione (6.7 g, 16.69 mmol, 91% yield).

Example 17

(R)-5-(2-(benzylamino)ethyl)-1-(6,8-difluorochroman-3-yl)-1H-imidazole-2(3H)-thione (Compound RY' Purified)

A suspension of (R)-5-(2-(benzylamino)ethyl)-1-(6,8-difluorochroman-3-yl)-1H-imidazole-2(3H)-thione (15 g, 37.4 mmol) in 2-butanone (MEK, 150 ml) was heated to 80° C. The resulting slurry was stirred for 2 hours at 80° C. and then slowly cooled to 20° C. over 2 hours. The solid was filtered, washed with 2-propanol (45 mL) and then dried in vacuum at 50° C. (R)-5-(2-(benzylamino)ethyl)-1-(6,8-difluorochroman-3-yl)-1H-imidazole-2(3H)-thione (12.6 g, 31.38 mmol, 84%) was obtained as an off white solid.

Example 18

N-benzyl-N-(4-hydroxy-3-oxobutyl)-2-nitrobenzenesulfonamide (Compound I)

Reaction of 1,1-dimethoxyacetone with dimethylformamide dimethyl acetal produced N,N-dimethyl enaminone which upon treatment with benzylamine gave N-benzyl enaminone. The latter was fully reduced to amino alcohol and N-protected with Ns-group. Acidic cleavage of acetal and simultaneous rearrangement afforded after chromatographic purification the target hydroxy ketone (Scheme 3).

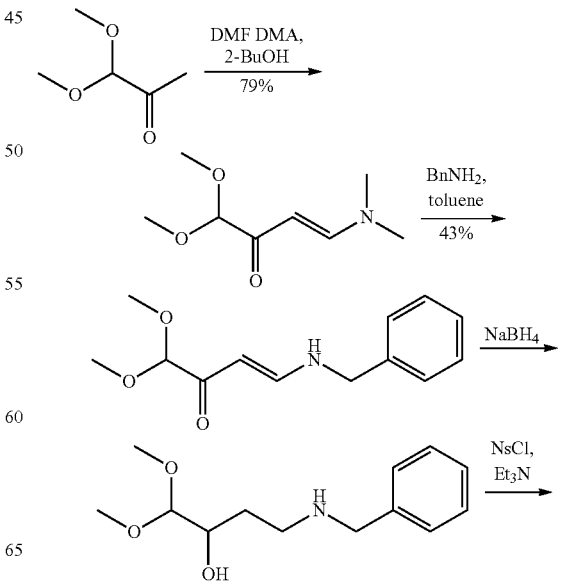

Scheme 3

31

-continued

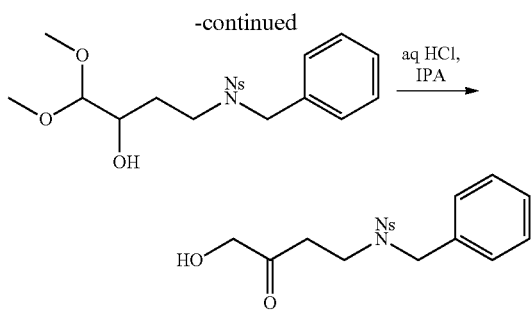

The steps were carried out as follows.

(a) (E)-4-(Dimethylamino)-1,1-dimethoxybut-3-en-2-one prepared as described in Maury et al, J. Heterocyclic Chem., 1978, 15, p. 1041

(b) (E)-4-(Benzylamino)-1,1-dimethoxybut-3-en-2-one

A mixture of (E)-4-(dimethylamino)-1,1-dimethoxybut-3-en-2-one (11 g, 63.5 mmol) and benzylamine (6.94 ml, 63.5 mmol) in toluene (130 ml) was stirred under reflux for 4 hours. Evaporated to dryness under vacuum, the residue was applied on a column, eluted with petroleum ether-ethyl acetate mixture 3:1, fractions collected to give (E)-4-(benzylamino)-1,1-dimethoxybut-3-en-2-one (6.4 g, 27.2 mmol, 42.8% yield) as dark yellow oil.

(c) 4-(Benzylamino)-1,1-dimethoxybutan-2-ol

To a solution of (E)-4-(benzylamino)-1,1-dimethoxybut-3-en-2-one (4.71 g, 20 mmol) in a mixture of 2-Propanol (60 ml) and Water (4.80 ml) was added sodium borohydride (3.03 g, 80 mmol) in portions at 20-25° C., the mixture was stirred overnight. Quenched with 5N HCl to pH 7 (approx 10 ml), pH adjusted to 8-9 with 5N NaOH, diluted with MTBE (100 ml) and brine (50 ml). Organic phase was dried (MgSO$_4$), evaporated, separated on a column with ethyl acetate-MeOH mixture 4:1, fractions collected to give 4-(benzylamino)-1,1-dimethoxybutan-2-ol (3.55 g, 14.83 mmol, 74.2% yield), colorless oil.

(d) N-Benzyl-N-(3-hydroxy-4,4-dimethoxybutyl)-2-nitrobenzenesulfonamide (without isolation of 4-(benzylamino)-1,1-dimethoxybutan-2-ol)

To a solution of (E)-4-(benzylamino)-1,1-dimethoxybut-3-en-2-one (1.176 g, 5 mmol) in a mixture of 2-Propanol (12.5 ml) and Water (1.200 ml) was added sodium borohydride (0.757 g, 20.00 mmol) in portions, the mixture was stirred for 7 hours. Quenched with 5N HCl to pH 7 (approx 2.5 ml), pH adjusted to 8-9 with 5N NaOH, diluted with MTBE (25 ml) and brine (15 ml). Organic phase was separated, triethylamine (0.767 ml, 5.50 mmol) was added with ice-cooling followed by 2-nitrobenzene-1-sulfonyl chloride (1.108 g, 5.00 mmol). The mixture was left at 0-5° C. (fridge) overnight. Washed with water, dried, evaporated to dryness, the residue applied on a column, eluted with petroleum ether-ethyl acetate mixture 1:1, fractions collected to give N-benzyl-N-(3-hydroxy-4,4-dimethoxybutyl)-2-nitrobenzenesulfonamide (1.9 g, 4.48 mmol, 90% yield), yellow oil.

32

(e) N-Benzyl-N-(4-hydroxy-3-oxobutyl)-2-nitrobenzenesulfonamide

To a solution of N-benzyl-N-(3-hydroxy-4,4-dimethoxybutyl)-2-nitrobenzenesulfonamide (0.212 g, 0.5 mmol) in 1-Propanol (1.5 ml) was added 37% hydrochloric acid (0.104 ml, 1.250 mmol) and the mixture was stirred at 90° C. in a weaton vial. Cooled, evaporated to dryness under vacuum, applied on a column in petroleum ether-ethyl acetate mixture 1:1, eluted with the same system. Fractions collected to give N-benzyl-N-(4-hydroxy-3-oxobutyl)-2-nitrobenzenesulfonamide (0.085 g, 0.225 mmol, 44.9% yield), yellowish oil.

Example 19

N-Benzyl-N-(4-hydroxy-3-oxobutyl)-2-nitrobenzenesulfonamide (Compound I)

Scheme 4

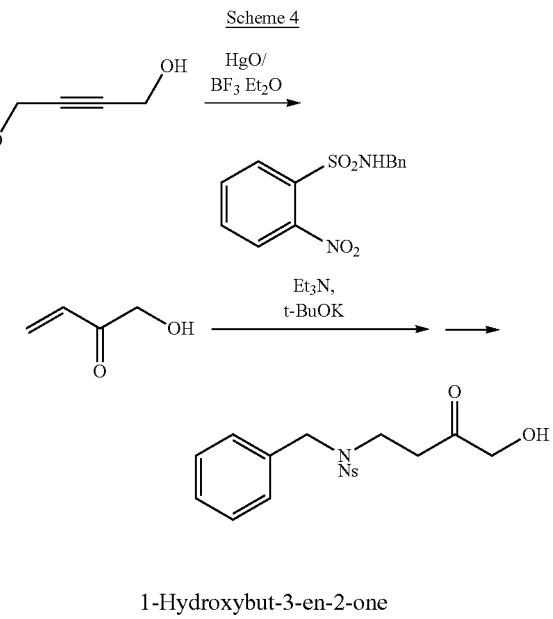

1-Hydroxybut-3-en-2-one

Prepared from but-2-yne-1,4-diol (Justus Liebigs Annalen der Chemie, 1955, v. 596, p. 38-78). Pd, Cu and Zn catalysts were used as alternatives to the Hg catalyst.

N-Benzyl-N-(4-hydroxy-3-oxobutyl)-2-nitrobenzenesulfonamide

To a solution of benzylamine (10.92 ml, 100 mmol) in DCM (150 ml) was added triethylamine (13.67 ml, 100 mmol) followed by a solution of 2-nitrobenzene-1-sulfonyl chloride (22.16 g, 100 mmol) in DCM (70 ml) at 5-10° C. with stirring. The mixture was stirred for 1 hour, stirring continued for 1 hour, washed with water, brine, most of DCM removed under reduced pressure. Ethyl acetate (150 ml) was added, another 25-30 ml distilled off under reduced pressure. To the resulting solution potassium tert-butoxide (0.561 g, 5.00 mmol) was added followed by 1-hydroxybut-3-en-2-one (9.47 g, 110 mmol) with stirring in one portion at 20-25° C. The mixture was stirred for 1 hour at 20-25° C., diluted with heptane (70 ml), washed with brine and 1N HCl (5 ml), organic phase was dried (MgSO$_4$), evaporated to dryness under reduced pressure. The resulting oil was purified on a column with ethyl acetate-petroleum ether mixture as eluent. Fractions containing the wanted product were collected and evaporated to dryness under reduced pressure to give N-benzyl-2-nitro-N-(4-hydroxy-3-oxobutyl)benzenesulfonamide (29.1 g, 77 mmol, 77% yield).

Example 20

N-benzyl-N-(4-hydroxy-3-oxobutyl)-ethyl methanoate (Compound I with Alternative Protecting Group—Ethyl Ethanoate Instead of Ns)

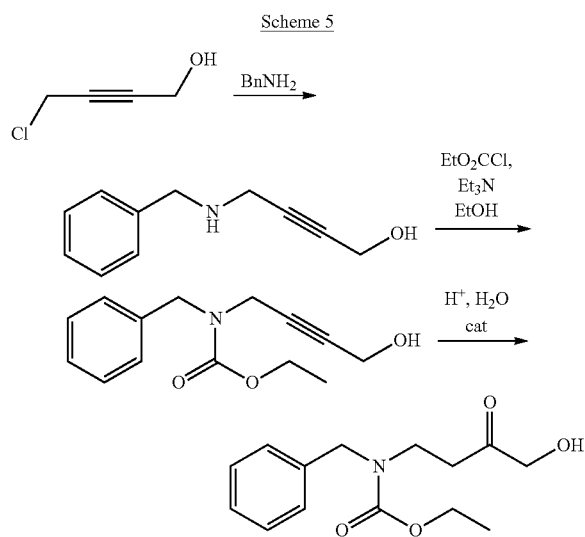

The steps were carried out as follows.

(a) Ethyl benzyl(4-hydroxybut-2-ynyl)carbamate

A mixture of benzylamine (2.185 ml, 20.00 mmol) and 4-chlorobut-2-yn-1-ol (1.045 g, 10.00 mmol) was stirred in EtOH (20 ml) for 1 hour under reflux. The mixture was cooled, evaporated to dryness under vacuum, the semi-solid residue was taken up into acetone (50 ml), the insoluble material was filtered off (benzylamine hydrochloride), the filtrate evaporated to dryness. The residue was dissolved in 96% EtOH (20 ml), triethylamine (4.18 ml, 30.0 mmol) was added followed by ethyl chloroformate (2.113 ml, 22.00 mmol) dropwise with ice-cooling and stirring. Allowed to warm up naturally with stirring during 1 hour, evaporated to dryness under vacuum, the residue was distributed between DCM (50 ml) and 1N HCl (25 ml). Organic phase was dried, evaporated to dryness, applied on a column, eluted with petroleum ether-ethyl acetate mixture 4:1=>2:1, fractions collected to give 2 g of less polar yellowish oil and 0.34 g of more polar oil. Less polar fraction was dissolved in ether, acidified with HCl/EtOH, diluted with (petroleum ether) PE (approx 1:1). Liquid was decanted from the separated oil and evaporated to dryness to give 1.6 g of oil. The oil was dissolved in MeOH (20 ml), 5N sodium hydroxide (2.000 ml, 10.00 mmol) added, stirred at 20-25° C. for 16 hours. Acidified to pH 6 with concentrated HCl, evaporated to dryness, taken up into DCM, organic phase dried, combined with more polar oil, separated on a column with petroleum ether-ethyl acetate mixture 4:1=>2:1. Fractions were collected under HPLC-MS control to give ethyl benzyl(4-hydroxybut-2-ynyl)carbamate (0.71 g, 2.87 mmol, 28.7% yield).

$^1$H NMR, 400 MHz, 20° C., CDCl$_3$) δ: 7.40-7.20 (5H, m), 4.59 (2H, s br), 4.24 (2H, m br), 4.22 (2H, t, J=7.1 Hz), 4.1-3.95 (2H, m br), 2.05, 1.95 (1H, 2 s br), 1.29 (3H, t br, J=7.0 Hz); $^{13}$C NMR (100 MHz, 20° C., CDC$_3$) δ: 156.1, 137, 128.5, 128.2, 127.7, 127.5, 82.1, 81.9, 80.8, 62, 51, 49.3, 35.8, 35.4, 14.6.

(b) Ethyl benzyl(4-hydroxy-3-oxobutyl)carbamate

A mixture of ethyl benzyl(4-hydroxybut-2-ynyl)carbamate (0.05 g, 0.202 mmol), mercury(II) acetate (6.44 mg, 0.020 mmol) and boron trifluoride etherate (5.12 µl, 0.040 mmol) in Acetonitrile (0.5 ml) and Water (0.250 ml) stirred at 90° C. in wheaton vial for 30 min. By HPLC-MS the main peak corresponds to expected product.

Example 21

(R)-6,8-difluorochroman-3-amine L-Tartrate salt (Compound JT')

The vessel was charged with (R)-methyl 6,8-difluorochroman-3-ylcarbamate (1.0 wt) and methanol (12.66 vol.), the content temperature was adjusted to 65° C. with stirring. A solution of potassium hydroxide (2.76 wt) in water (4.15 vol.) was transferred to the vessel while maintaining 65° C. and the mixture was stirred for 24 hours. The content was adjusted to 35° C., water (5.6 vol.) was charged and the vessel was set up for atmospheric distillation. The content was distilled off at 70° C. internal temperature and 80° C. in doubled jacket until a residual volume reached 8-10 vol. The content adjusted to 30° C., dichloromethane (6.5 vol.) was charged while cooling the content temperature to 20/25° C. Stirred for 15 min, settled for 15 min, the lower organic phase was separated. Dichloromethane (3.0 vol.) was charged, the mixture stirred for 15 min, settled for 15 min, the lower organic phase was separated. Combined organic phase was washed twice with brine and transferred to a vessel set up for vacuum distillation. The vessel was charged with ethanol (20.0 vol.), 4.3 vol. of distillate was distilled off. The vessel was set up for atmospheric distillation; content of the vessel was distilled off at 65/75° C. internal temperature and 90° C. in doubled jacket until vessel volume was 20.0 vol. and then distilled at constant volume by the addition of ethanol until refractive index showed no dichloromethane was present. A solution of L-tartaric acid (0.647 wt, 1.108 eq) in water (3.0 vol.) was prepared and adjusted to 70° C. The solution was added slowly to previously obtained ethanolic solution at 75° C. The mixture stirred at 75° C. for 5 hours then cooled to 0° C. at 10° C./hour. The content was stirred at 0° C. for 12 hours, ethanol (2.5 vol.) was charged and the temperature was adjusted to 0° C. The content of the vessel was transfer to a filter. The filter cake was washed with ethanol (5.0 vol. and 2.5 vol.) and dried under vacuum at 45° C. Yield of (R)-6,8-difluorochroman-3-amine L-Tartrate salt 90% of theory.

$^1$H NMR (400 MHz, DMSO, 20° C.) δ: 7.14 (1H, m, J=3.0, 8.9 and 11.5), 6.92 (1H, d br, J=9.3), 4.24 (1H, dd, J=2.4 and 11.3), 4.17 (1H, dd, J=5.6 and 11.2), 4.02 (2H, s), 3.72 (1H, m), 3.17 (1H, dd, J=5.7 and 17.5), 2.84 (1H, dd, J=5.3 and 17.5); $^{13}$C NMR (100 MHz, DMSO, 20° C.) δ: 174.6, 155.1 (dd, J=11.5 and 239.0), 150.3 (dd, J=13.0 and 246.0), 138.5 (dd, J=3.3 and 11.5), 122.9 (dd, J=2.5 and 9.5), 111.3 (dd, J=3.5 and 23.0), 102.9 (dd, J=22.5 and 27.5), 72.1, 66.7, 42.7, 28.7.

It will be appreciated that the invention described above may be modified within the scope of the attached claims.

The invention claimed is:

1. A process for preparing a compound of formula RY or a pharmaceutically acceptable salt thereof,

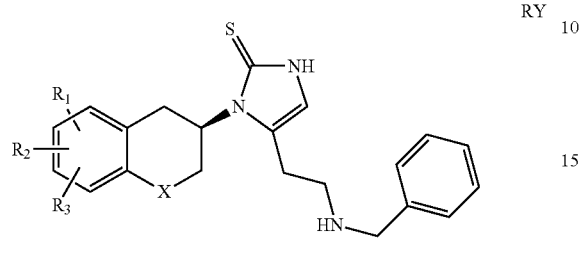

RY wherein, $R_1$, $R_2$ and $R_3$ are the same or different and signify hydrogen, halogen, alkyl, nitro, amino, alkylcarbonylamino, alkylamino or dialkylamino group; and X signifies $CH_2$, an oxygen atom or a sulphur atom;

which process comprises reducing a compound of formula D,

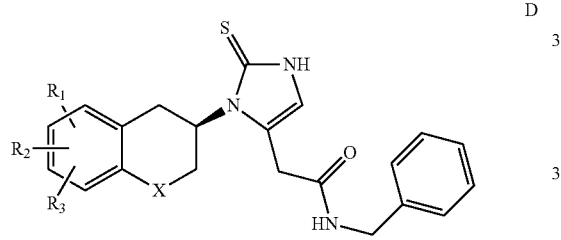

D wherein $R_1$, $R_2$, $R_3$ and X are as hereinbefore defined in formula RY;

and optionally thereafter converting the compound RY to a pharmaceutically acceptable salt thereof.

2. A process according to claim 1, wherein compound RY has the formula RY′

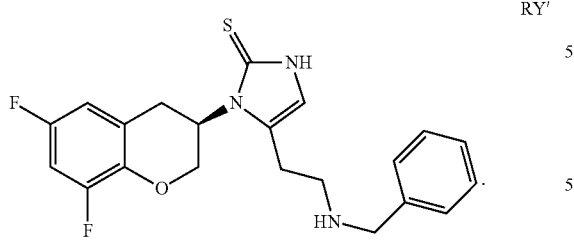

RY′

3. A process according to claim 1, wherein the reduction of compound D to the compound RY is carried out using a reducing agent comprising a $NaBH_4$—$BF_3$.complex.

4. A process according to claim 3, wherein the $NaBH_4$—$BF_3$.complex is $NaBH_4$—$BF_3$.THF.

5. A process according to claim 1, wherein the compound of formula D is prepared by condensing a compound of formula C,

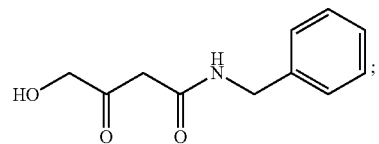

C with a compound of formula JT,

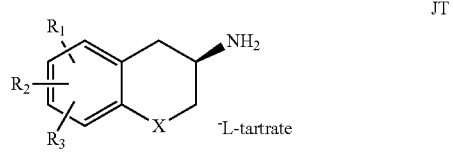

JT wherein $R_1$, $R_2$, $R_3$ are the same or different and signify hydrogen, alkyl, nitro, amino, alkylcarbonylamino, alkylamino or dialkylamino group, and X signifies $CH_2$, an oxygen atom or a sulphur atom.

6. A process for preparing a compound of formula RY or a pharmaceutically acceptable salt thereof according to claim 1, the process comprising: brominating a compound of formula A to form a compound of formula B; hydroxylation of compound B to the compound of formula C; cyclising the compound C to form the compound of formula D; and reducing the compound D to form the compound of formula RY, and optionally converting compound RY to a pharmaceutically acceptable salt thereof

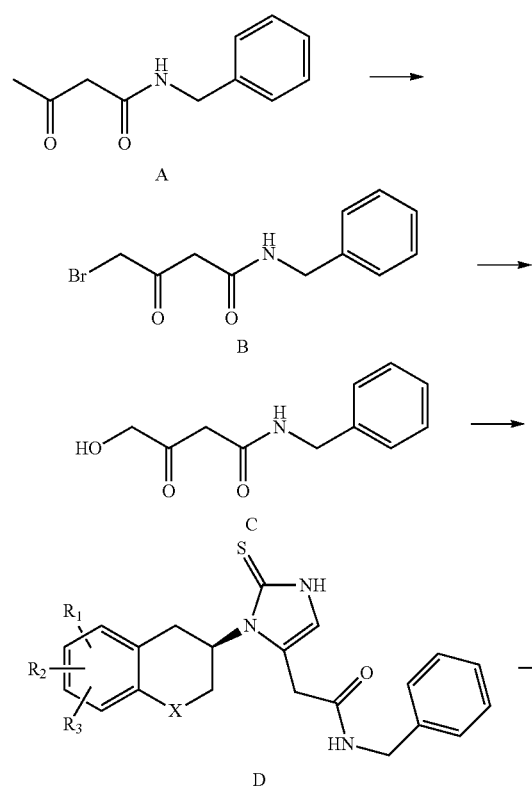

-continued

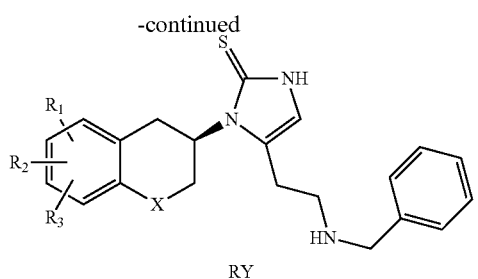

RY wherein $R_1$, $R_2$, $R_3$ are the same or different and signify hydrogen, halogen, alkyl, nitro, amino, alkylcarbonylamino, alkylamino or dialkylamino group; and X signifies $CH_2$, an oxygen atom or a sulphur atom.

7. A process according to claim 1, wherein X is O.
8. A process according to claim 1, wherein one of $R_1$, $R_2$, $R_3$ is hydrogen and the others are fluorine.
9. A process according to claim 1, wherein compound D has the formula D'

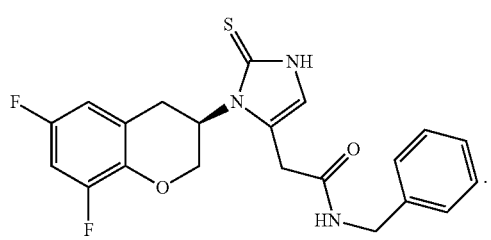

D'

10. A process according to claim 3, wherein X is O.
11. A process according to claim 3, wherein one of $R_1$, $R_2$, $R_3$ is hydrogen and the others are fluorine.
12. A process according to claim 3, wherein compound D has the formula D'

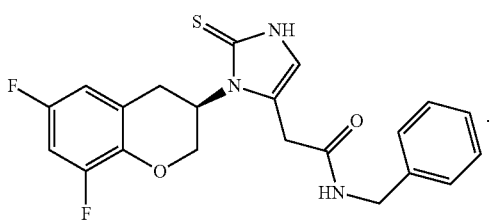

D'

13. A process according to claim 3, wherein the $NaBH_4$—$BF_3$.complex is $NaBH_4$—$BF_3.Et_2O$.
14. A process according to claim 4, wherein X is O.
15. A process according to claim 4, wherein one of $R_1$, $R_2$, $R_3$ is hydrogen and the others are fluorine.
16. A process according to claim 4, wherein compound D has the formula D'

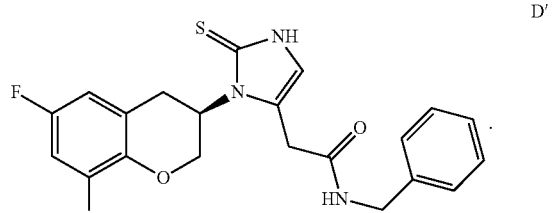

D'

17. A process according to claim 1, wherein the reduction of compound D to the compound RY is carried out using a reducing agent comprising sodium bis(methoxyethoxy)aluminohydride), Borane-THF complex, or $NaBH_4$-methanesulfonic acid.
18. A process according to claim 6, wherein X is O.
19. A process according to claim 6, wherein one of $R_1$, $R_2$, $R_3$ is hydrogen and the others are fluorine.
20. A process according to claim 6, wherein compound D has the formula D'

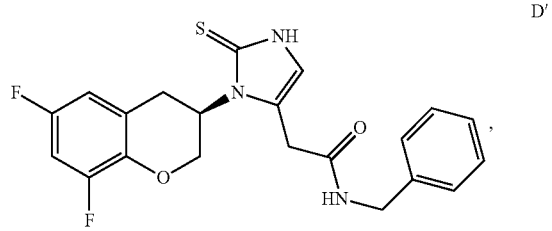 [SMILES: O=C(Cc1c[nH]c(=S)n1[C@H]1COc2c(F)cc(F)cc2C1)NCc1ccccc1]

D' and
wherein compound RY has the formula RY'

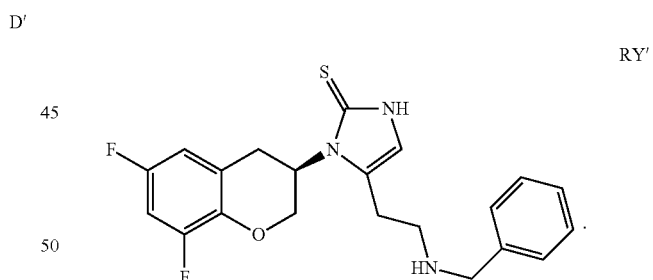

RY'

* * * * *

UNITED STATES PATENT AND TRADEMARK OFFICE
CERTIFICATE OF CORRECTION

PATENT NO.       : 9,346,751 B2
APPLICATION NO.  : 14/127231
DATED            : May 24, 2016
INVENTOR(S)      : Alexander Beliaev et al.

It is certified that error appears in the above-identified patent and that said Letters Patent is hereby corrected as shown below:

In the Specification

Column 1, line 60, replace "p-blocker" with --β-blocker--.

Column 2, line 7, replace "disulfuram" with --disulfiram--.

Column 19, line 25, replace "phenyloin" with --phenytoin--.

Column 19, line 58, replace "inaminone" with --inamrinone--.

In the Claims

Claim 5, column 36, line 22, after "hydrogen" insert --halogen,--.

Signed and Sealed this
Second Day of August, 2016

Michelle K. Lee
*Director of the United States Patent and Trademark Office*